US012700483B2

(12) United States Patent
Martin et al.

(10) Patent No.: US 12,700,483 B2
(45) Date of Patent: **\*Aug. 4, 2026**

(54) FILTERING DATA FROM AN ANALYTICAL DEVICE

(71) Applicant: Roche Diagnostics Operations, Inc., Indianapolis, IN (US)

(72) Inventors: Stephen Martin, Zug (CH); Alexandra Paun, Zurich (CH); Jakub Winiarz, Zug (CH)

(73) Assignee: Roche Diagnostics Operations, Inc., Indianapolis, IN (US)

( \* ) Notice: Subject to any disclaimer, the term of this patent is extended or adjusted under 35 U.S.C. 154(b) by 0 days.

This patent is subject to a terminal disclaimer.

(21) Appl. No.: 18/666,264

(22) Filed: May 16, 2024

(65) Prior Publication Data

US 2024/0305571 A1 Sep. 12, 2024

Related U.S. Application Data

(63) Continuation of application No. 17/360,539, filed on Jun. 28, 2021, now Pat. No. 12,021,752.

(30) Foreign Application Priority Data

Jul. 6, 2020 (EP) ..................................... 20184222

(51) Int. Cl.
*G16H 10/40* (2018.01)
*H04L 41/0894* (2022.01)
(Continued)

(52) U.S. Cl.
CPC ......... *G16H 10/40* (2018.01); *H04L 41/0894* (2022.05); *H04L 43/062* (2013.01); *H04L 47/24* (2013.01)

(58) Field of Classification Search
CPC ....... H04L 47/24; H04L 43/062; H04L 41/22; H04L 41/0894; H04L 51/212;
(Continued)

(56) References Cited

U.S. PATENT DOCUMENTS 8,688,225 B2 4/2014 Panken et al.
2003/0046421 A1\* 3/2003 Horvitz ................... H04L 51/00
709/206

(Continued)

FOREIGN PATENT DOCUMENTS

CN 104081375 10/2014
CN 110998740 4/2020
(Continued)

OTHER PUBLICATIONS

Search Report issued Jun. 17, 2024, in Chinese Application No. 2021107596612, 3 pp.
(Continued)

*Primary Examiner* — Anh Nguyen
(74) *Attorney, Agent, or Firm* — Lee & Hayes, P.C.

(57) ABSTRACT

A computer-implemented method generates a message filter configuration based on a message priority indication of analytical device status messages received from a first analyzer network, the configuration based on identifying a type of analytical device status data associated with the message priority indication. The method includes communicating the message filter configuration, or a portion thereof, to a second analyzer network comprising a second analytical device.

18 Claims, 12 Drawing Sheets

(51) Int. Cl.
_H04L 43/062_ (2022.01)
_H04L 47/24_ (2022.01)

(58) Field of Classification Search
CPC ...... H04L 51/226; G16H 10/40; G16H 40/40;
G16H 40/67; G16H 10/60; G16H 80/00;
G16H 50/20; G16H 50/30; G06F 9/5038;
G06F 16/23
See application file for complete search history.

(56) References Cited

U.S. PATENT DOCUMENTS

| | | | |
|---|---|---|---|
| 2007/0156886 A1 | 7/2007 | Srivastava | |
| 2009/0098859 A1* | 4/2009 | Kamdar ................ | H04L 51/214 |
| | | | 455/412.1 |
| 2010/0088378 A1 | 4/2010 | Asawa et al. | |
| 2016/0307100 A1* | 10/2016 | Cooper ................ | G06F 3/0484 |
| 2017/0134474 A1* | 5/2017 | Gao ........................ | H04L 67/62 |
| 2017/0178482 A1 | 6/2017 | Pan et al. | |
| 2019/0075069 A1 | 3/2019 | Kumar et al. | |
| 2019/0110764 A1* | 4/2019 | Murai .................. | A61B 5/0002 |
| 2020/0159957 A1* | 5/2020 | Reimers .............. | G06F 21/6245 |
| 2021/0304881 A1* | 9/2021 | White ................... | G16H 40/20 |

FOREIGN PATENT DOCUMENTS

| | | |
|---|---|---|
| CN | 111093759 | 5/2020 |
| CN | 111192674 | 5/2020 |
| EP | 3091457 B1 | 10/2018 |
| JP | H07-183932 A | 7/1995 |
| JP | 2003-248647 A | 9/2003 |
| JP | 2011-113492 A | 6/2011 |
| JP | 2011-145898 A | 7/2011 |
| JP | 2012-252589 A | 12/2012 |
| JP | 2016212865 | 12/2016 |
| WO | 2013/074267 A1 | 5/2013 |
| WO | 2016/188738 A1 | 12/2016 |
| WO | 2018/091492 A1 | 5/2018 |
| WO | 2019/010133 A1 | 1/2019 |
| WO | 2019/020587 A1 | 1/2019 |

OTHER PUBLICATIONS

European Search Report issued Dec. 8, 2020, in Application No. 20184222.6, 2 pp.
Notice of Allowance issued Jun. 20, 2023, in Application No. JP 2021-111547, 3 pp.

* cited by examiner

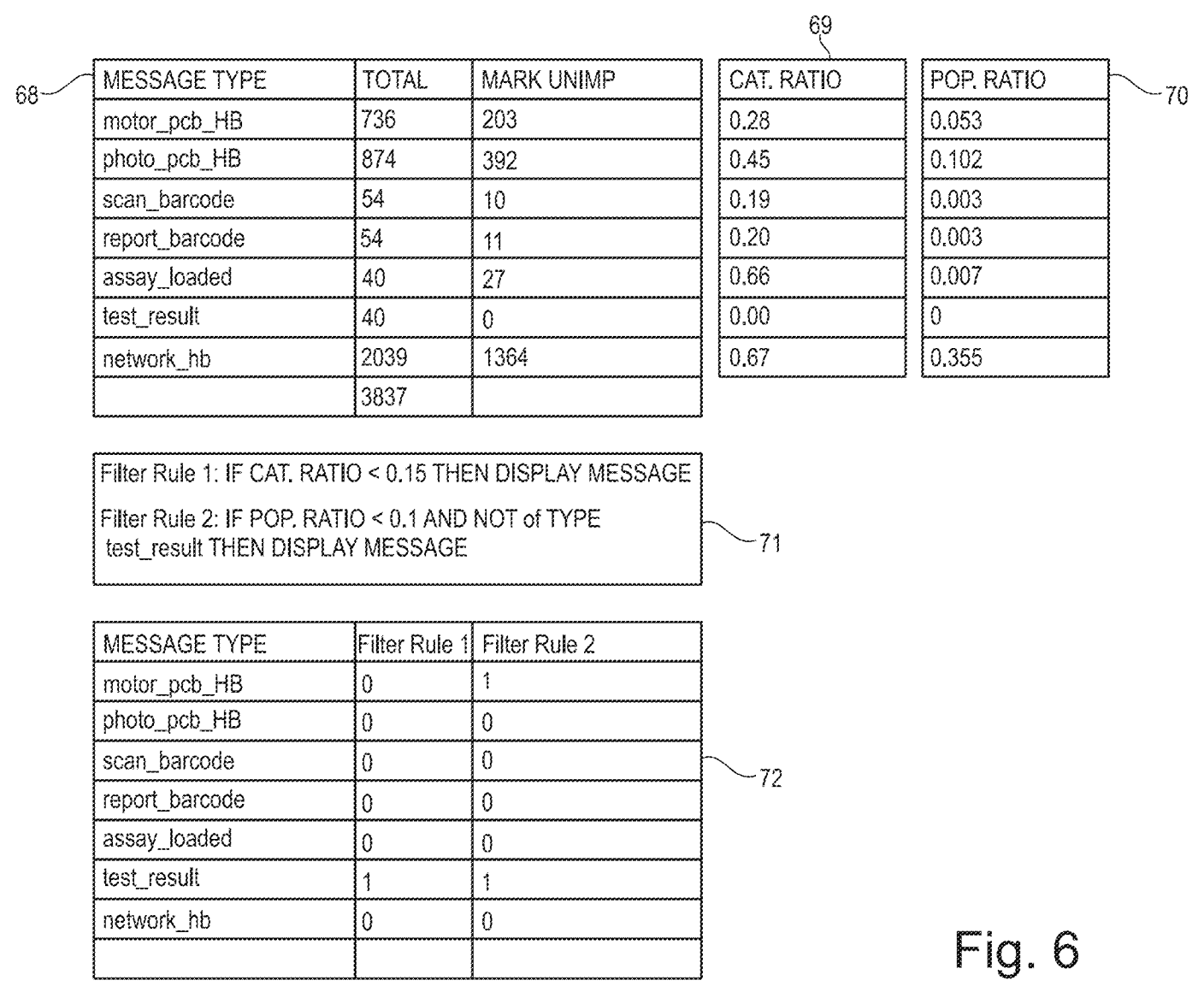

68

| MESSAGE TYPE | TOTAL | MARK UNIMP |
|---|---|---|
| motor_pcb_HB | 736 | 203 |
| photo_pcb_HB | 874 | 392 |
| scan_barcode | 54 | 10 |
| report_barcode | 54 | 11 |
| assay_loaded | 40 | 27 |
| test_result | 40 | 0 |
| network_hb | 2039 | 1364 |
| | 3837 | |

69

| CAT. RATIO |
|---|
| 0.28 |
| 0.45 |
| 0.19 |
| 0.20 |
| 0.66 |
| 0.00 |
| 0.67 |

70

| POP. RATIO |
|---|
| 0.053 |
| 0.102 |
| 0.003 |
| 0.003 |
| 0.007 |
| 0 |
| 0.355 |

71

Filter Rule 1: IF CAT. RATIO < 0.15 THEN DISPLAY MESSAGE

Filter Rule 2: IF POP. RATIO < 0.1 AND NOT of TYPE test_result THEN DISPLAY MESSAGE

72

| MESSAGE TYPE | Filter Rule 1 | Filter Rule 2 |
|---|---|---|
| motor_pcb_HB | 0 | 1 |
| photo_pcb_HB | 0 | 0 |
| scan_barcode | 0 | 0 |
| report_barcode | 0 | 0 |
| assay_loaded | 0 | 0 |
| test_result | 1 | 1 |
| network_hb | 0 | 0 |

Fig. 6

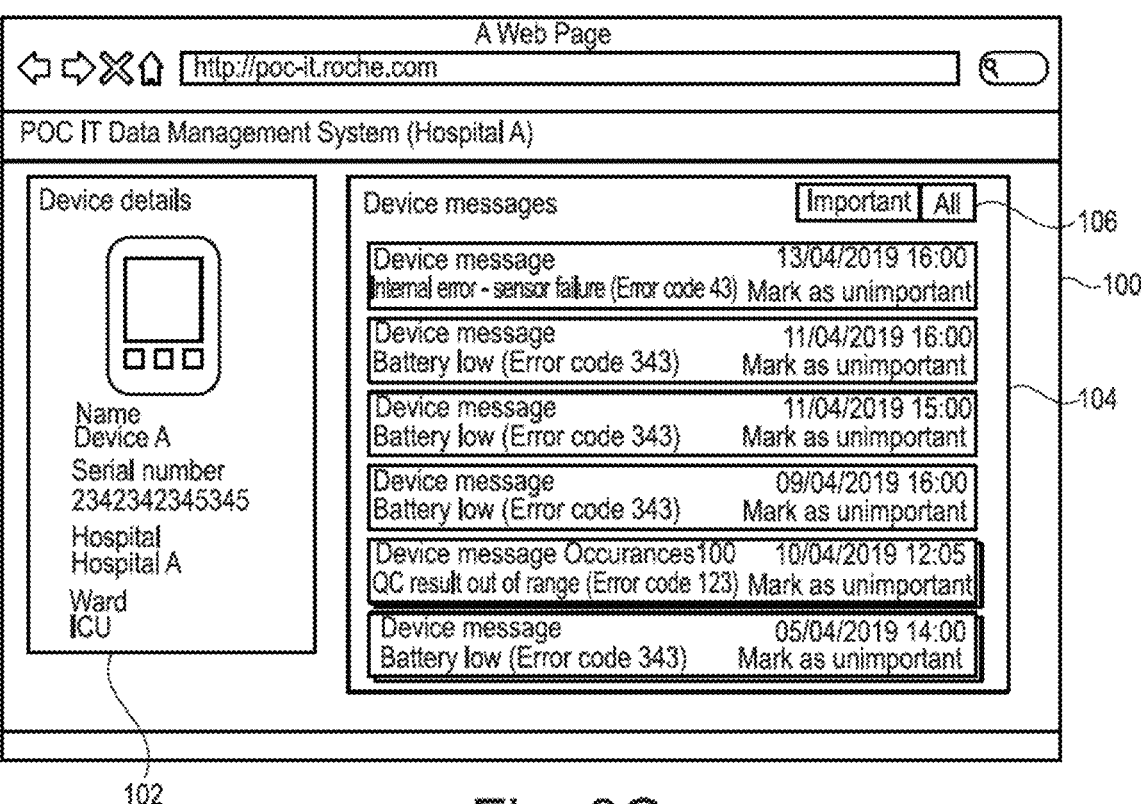

A Web Page http://poc-it.roche.com

POC IT Data Management System (Hospital A)

Device details

Name
Device A

Serial number
2342342345345

Hospital
Hospital A

Ward
ICU

Device messages     | Important | All |

| Device message | 13/04/2019 16:00 |
| Internal error - sensor failure (Error code 43) | Mark as unimportant |

| Device message | 11/04/2019 16:00 |
| Battery low (Error code 343) | Mark as unimportant |

| Device message | 11/04/2019 15:00 |
| Battery low (Error code 343) | Mark as unimportant |

| Device message | 09/04/2019 16:00 |
| Battery low (Error code 343) | Mark as unimportant |

| Device message Occurances100 | 10/04/2019 12:05 |
| QC result out of range (Error code 123) | Mark as unimportant |

| Device message | 05/04/2019 14:00 |
| Battery low (Error code 343) | Mark as unimportant |

A Web Page http://poc-it.roche.com

POC IT Data Management System (Hospital B)

Device details

New

Name
Device B

Serial number
6778678678

Hospital
Hospital B

Ward
Diabetes ward

Device messages - smart defaults

Do you want to download smart default
configuration of device messages types?

| Cancel | Continue |

FILTERING DATA FROM AN ANALYTICAL DEVICE

CROSS-REFERENCE TO RELATED APPLICATIONS

This application is a continuation of U.S. application Ser. No. 17/360,539, filed Jun. 28, 2021, which claims priority to EP application Ser. No. 20/184,222.6, filed Jul. 6, 2020, the disclosures of which are hereby incorporated by reference in their entirety.

BACKGROUND

The present disclosure generally relates to a computer-implemented method for generating a message filter configuration based on a message priority indication received from a first analyzer network, and associated apparatuses, a networked system, a computer program element and a computer readable medium.

In clinical care environments, analytical devices of medical samples can be used at, or near to, the point of care. Such analytical devices are designated "Point of Care (POC) testing devices". The analytical devices can communicate a variety of status messages containing information about the technical status of the testing devices with a central server, for example.

POC devices (analytical devices) send a large number of device messages (analytical device status data) denoting, for example, events, analysis results, or other analytical device status information to a POC IT data management system.

A typical POC device generates a significant number of device messages. Consequently, the coherent monitoring of information concerning the status of a large number of POC devices can be challenging. Therefore, such POC devices and their management systems can be further improved.

SUMMARY

According to the present disclosure, a system and computer implemented method for generating a message filter configuration based on a message priority indication received from a first analyzer network are presented. The first analyzer network can comprise at least one analytical device configured to generate analytical device status data. The method can comprise receiving, at a data processing agent, a message priority indication indicating a priority assigned to the analytical device status data in the first analyzer network, providing, at the data processing agent, at least one message filter configuration based on the message priority indication of the analytical device status data, and communicating the message filter configuration, or a portion thereof, to a second analyzer network comprising a second analytical device.

Other features of the embodiments of the present disclosure will be apparent in light of the description of the disclosure embodied herein.

BRIEF DESCRIPTION OF THE SEVERAL VIEWS OF THE DRAWINGS

The following detailed description of specific embodiments of the present disclosure can be best understood when read in conjunction with the following drawings, where like structure is indicated with like reference numerals and in which:

FIG. 6 illustrates schematically an example of generating a message filter configuration based on a message priority indication of analytical device status data according to an embodiment of the present disclosure.

FIG. 9C illustrates schematically further GUI features of an analytical device management system (POC-DMS) according to an embodiment of the present disclosure.

FIG. 10A illustrates schematically the installation of a message filter configuration on an analytical device management system (POC-DMS) according to an embodiment of the present disclosure.

DETAILED DESCRIPTION

Figure 1:
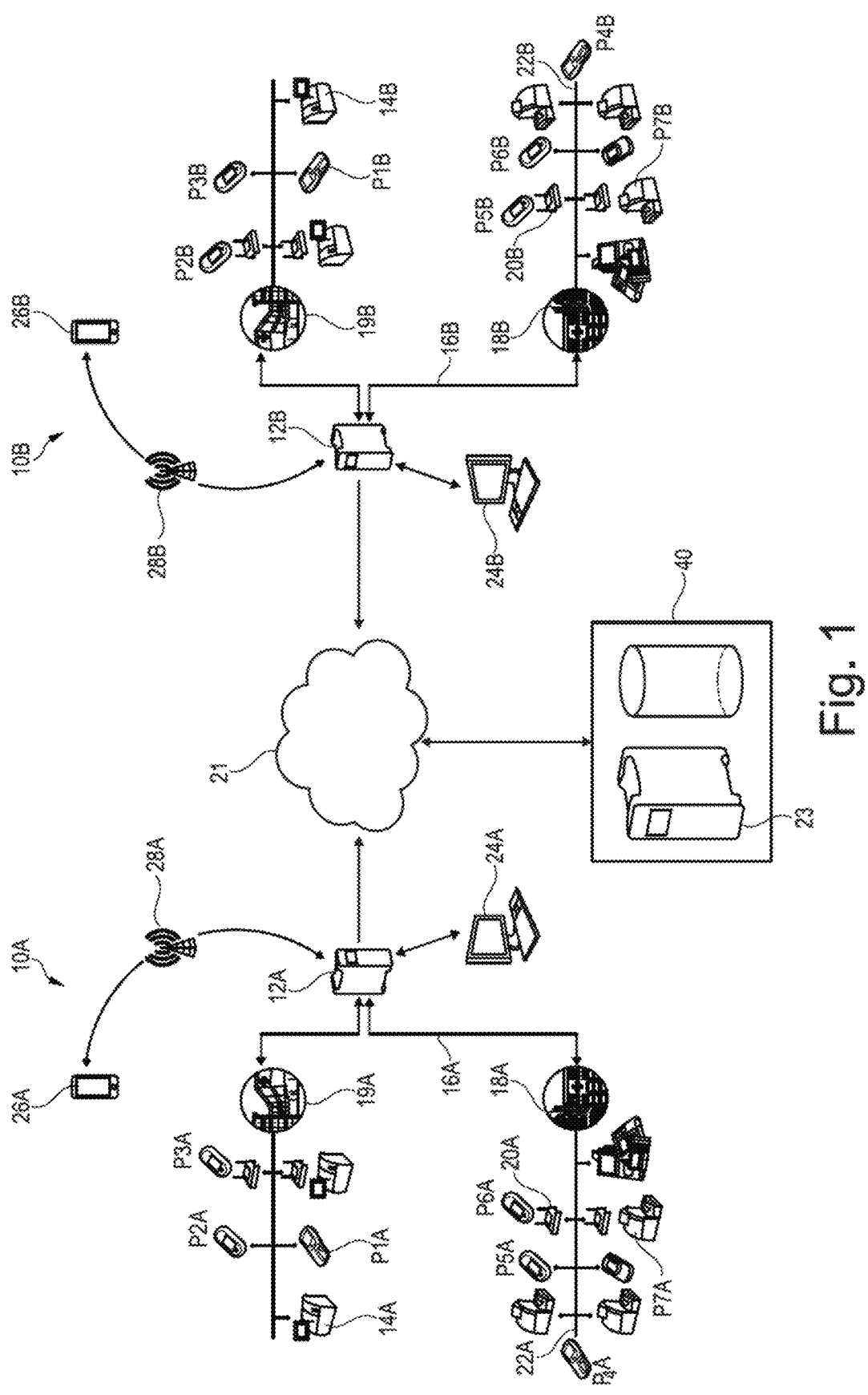
FIG. 1 illustrates schematically a networked system for analytical device management according to an embodiment of the present disclosure.

In the following detailed description of the embodiments, reference is made to the accompanying drawings that form a part hereof, and in which are shown by way of illustration, and not by way of limitation, specific embodiments in which the disclosure may be practiced. It is to be understood that other embodiments may be utilized and that logical, mechanical and electrical changes may be made without departing from the spirit and scope of the present disclosure.

A computer implemented method for generating a message filter configuration based on a message priority indication received from a first analyzer network is provided. The first analyzer network can comprise at least one analytical device configured to generate analytical device status data. The method can comprise receiving, at a data processing agent, a message priority indication indicating a priority assigned to the analytical device status data in the first analyzer network, providing, at the data processing agent, at least one message filter configuration based on the message priority indication of the analytical device status data, and communicating the message filter configuration, or a portion thereof, to a second analyzer network comprising a second analytical device.

An effect of this can be that the message viewing preferences of a large number of users of analytical devices can be captured and used to generate a message filter configuration that can be applied to filter analytical device status data appearing on other analytical devices and their management systems. The analytical device status data capture and filtering can occur, and be updated automatically and continuously, to reflect changes in user behavior or a reaction to the generation of analytical device status data based on a change in context of an analyzer that generates a given message.

This can have the effect of enabling important analytical device status data about the internal state of an analytical device to be reported to a user more clearly. Typically, a typical analytical device system can contain many analytical devices and thousands of items of analytical device status data can be generated per hour.

The approach introduced herein can enable a message filter to be applied based on user inputs received from a user interface of one or more point-of-care (POC) data management systems or analyzers. Following filtering, analytical device status data concerning the internal state of a POC analyzer that are likely to be important can be more prominently displayed.

A data processing agent (server) that is communicatively coupled to a POC data management system and/or mobile display device may encounter capacity constraints when attempting to push (transmit) a large number of messages to be displayed on a graphical user interface (GUI) of the POC data management system and/or mobile display device. In an example, modern web display frameworks employ one or more data bindings between the data processing agent (server) and the GUI in the POC data management system and/or mobile display device.

The performance of the data processing agent (server) can be improved when the number of messages displayed at the POC data management system and/or mobile display device are reduced, because, in an example, fewer data bindings between the GUI and the data processing agent (server) need to be serviced simultaneously. In particular, the data processing agent (server) may experience a reduction in the use of working memory (RAM) and a reduction in communication latency with the POC data management system and/or mobile display device. In particular, a mobile device servicing the data bindings may experience an improvement in battery life.

A further effect can be that the operation of a POC data management system or mobile device may be simplified. For example, a POC data management system may maintain a database of analytical device status data that grows at a rate of hundreds, thousands, or even tens of thousands of messages per hour. In the POC data management system, the analytical device status data may be displayed as a list of message boxes, optionally in an "infinite feed" enabling user scrolling through the list of messages.

The management of such a feed of messages with a constantly increasing number of messages can be a technical concern because currently, all of the messages that need to be displayed on the feed must be cached in working memory, handled by the GUI display software and ultimately loaded in the video buffer of the POC data management system as the user scrolls in the GUI of the POC data management system.

As the message feed increases in size, the amount of data to be switched between working memory, the video buffer, and the GUI of the POC data management system grows. This results in more computational effort to display the message feed to a user, and thus in greater power consumption at the POC data management system, and increased latency when displaying a scrollable feed of analytical device status data. The problem can be compounded when the POC data management system is hosted or accessed from a portable device, such as a smartphone or a computer tablet; owing to a need to transmit a large data display feed of a POC data management system GUI over a wireless data connection which may be restricted in bandwidth, latency control, or reliability.

According to the technique of the present specification, fewer low relevance items of analytical device status information may need to be cached for display on the GUI, when the GUI is operated in a display mode that only displays messages having a higher relevance. The message filter discussed herein can be automatically generated to select the most relevant messages for a given class of user or context according to many message priority indications applied to the analytical device status data. The messages of high relevance may be stored in short-term memory such as random access memory (RAM) or another low latency memory store. The messages of lower relevance may be stored in non-volatile memory.

Although the GUI software discussed herein can have an option to display all analytical device status data, there can be an option to display only the most relevant messages, leading to a more responsive display and a much reduced working memory requirement of the associated GUI software operating on the POC data management system, even whilst displaying messages of high relevance.

An apparatus configured to host a data processing agent for processing data from an analytical device is also provided. The apparatus can comprise a communications interface, a data memory, and a processor coupled to the communications interface and the data memory.

The communications interface can be configured to receive one or more items of data comprising a priority indication transmitted from the first analytical device management system to the data processing agent via a communications network.

The processor can be configured to receive, from the communications interface, the message priority indication indicating a priority assigned to an item of analytical device status data, and to generate or update, a message filter configuration stored in the data memory based on the assigned message priority.

The communications interface can further be configured to communicate the message filter configuration, or a portion thereof, to a second analyzer network comprising a second analytical device.

A networked system for analytical device management can also be provided. The network system can comprise a first set of one or more analytical devices configured to analyze patient medical samples and to generate analytical device status data, a first analytical device management system configured to receive at least one analyzer messages from one or more analytical devices comprised in the first set of one or more analytical devices, an apparatus configured to host a data processing agent for processing data received from the first analytical device management system and/or the first set of one or more analytical devices, a second set of one or more analytical devices configured to analyze patient medical samples, a second analytical device management system configured to receive at least one analyzer message from one or more analytical devices comprised in the second set of one or more analytical devices, and a communication network configured to communicatively connect the first analytical device management system, the apparatus configured to host the data processing agent, and second analytical device management system.

The apparatus can be configured to receive a message priority indication generated by the first analytical device management system and/or the at least one analytical device in the first analyzer network, indicating a priority assigned to the analytical device status data. The apparatus can be configured to generate or to update a message filter configuration based on the message priority of the analytical device status data. The apparatus can be configured to communicate the message filter configuration, or a portion thereof, to the second analytical device management system and/or the second set of one or more analytical devices. The second analytical device management system and/or at least one analytical device in the second set of one or more analytical devices can be configured to receive a further message from within the second analyzer network, and to display the further message according to the priority assigned in the received message filter configuration.

A computer program element comprising computer-readable instructions for controlling an apparatus according to the above apparatus which, when being executed by a processing unit of the apparatus, can be adapted to perform the above method.

A computer readable medium or signal having stored, or encoded thereon, the computer program element of the networked system is also provided.

A method of operating an analytical device management system and/or analytical devices can be configured to receive a plurality of items of analytical device status data from at least one analytical device in a second analyzer network, request, via a communications network, from the apparatus, a message filter configuration configured to filter at least one of the plurality of items of analytical device status data received from the second analyzer network, receive, via the communications network, the message filter configuration from the apparatus, and filter at least one item of analytical device status data in the plurality of items of analytical device status data according to the message filter configuration to generate a filtered plurality of messages.

According to an embodiment of the above method, the method can further comprise displaying, via a user interface of the analytical device management system, the filtered plurality of items of analytical device status data.

Another apparatus is provided. The apparatus can be configured to host an analytical device management system for processing data from one or more analytical devices of medical samples. The apparatus can comprise a communications interface, a data memory, and a processor coupled to the communications interface and the data memory.

The communications interface can be configured to receive a plurality of items of analytical device status data from at least one analytical device in a second analyzer network, and to request, via a communications network, from an apparatus according to the second aspect, a message filter configuration configured to filter at least one of the plurality of messages received from the second analyzer network. The communications interface can be configured to receive, via the communications network, the message filter configuration from the apparatus according to the second aspect and to store it in the data memory. The processor can be configured to filter at least one item of analytical device status data in the plurality of items of analytical device status data according to the message filter configuration stored in the data memory to generate a filtered plurality of messages.

As used herein, the terms "comprises", "comprising", "includes", "including", "has", "having", or any other variation thereof, are intended to cover a non-exclusive inclusion.

The terms "patient sample" and "biological sample" can refer to material(s) that may potentially contain an analyte of interest. The patient sample can be derived from any biological source, such as a physiological fluid, including blood, saliva, ocular lens fluid, cerebrospinal fluid, sweat, urine, stool, semen, milk, ascites fluid, mucous, synovial fluid, peritoneal fluid, amniotic fluid, tissue, cultured cells, or the like. The patient sample can be pretreated prior to use, such as preparing plasma from blood, diluting viscous fluids, lysis or the like. Methods of treatment can involve filtration, distillation, concentration, inactivation of interfering components, and the addition of reagents. A patient sample may be used directly as obtained from the source or used following a pretreatment to modify the character of the sample. In some embodiments, an initially solid or semisolid biological material can be rendered liquid by dissolving or suspending it with a suitable liquid medium. In some embodiments, the sample can be suspected to contain a certain antigen or nucleic acid.

The term "analytical device" as used herein can encompass any apparatus for obtaining measurement values relating to a medical condition of a patient.

In one example, the analytical device may be an automated analyzer of medical samples for obtaining a measurement value relating to a medical condition of a patient. For example, an analytical device may measure light absorption, fluorescence, electrical potential or other physical or chemical characteristics of the reaction to provide the measurement value. Often such patient samples can be treated before analytical testing is done. Blood sampled from a patient can be e.g., centrifuged to obtain serum or treated with anticoagulants to obtain plasma.

Analytical testing by an analyzer can have the goal of determining the presence and/or concentration of an analyte in a patient sample. The term "analyte" can be a general term for substances for which information about presence and/or concentration is intended. Examples of analytes are e.g., glucose, coagulation parameters, endogenic proteins (e.g., proteins released from the heart muscle), metabolites, nucleic acids and so on.

Alternatively, the analytical device can be a handheld or mobile device comprising sensors configured to acquire measurement values from a patient.

An "analytical device" may comprise a portable appliance that can be communicatively connected to a smartphone, tablet PC, or other computing device via a USB™, WiFi™, or Bluetooth™ connection, for example. Such a portable appliance may be configured to perform analytical testing.

A measurement value may comprise data collected from, for example, the sensors of a smartphone. By way of example only, a measurement value may be data obtained by a smartphone accelerometer that characterizes a degree of patient tremor. A measurement value may be a photograph of a dermatological condition obtained using a smartphone camera. A measurement value may be a sound recording obtained using a smartphone microphone. A measurement value may be a video obtained using a smartphone for the purposes of assessing patient gait, for example. In this way, standard features of smartphones, tablet PCs, or other computing devices may perform the function of an analytical device. An application executed on a smartphone, or other computing device, can be capable of obtaining such data and communicating it to a data processing agent.

An "analytical device" may be configured so as to be usable in the vicinity of a patient ward, in which case it is often referred to as a "Point of Care (POC) device". However, the techniques discussed herein are not limited to POC devices and may be applied to many types of laboratory analysis system that generate message data.

The term "patient health parameter" as used herein can encompass any aspect of a patient's physiology that can be measurable or indicated by an analysis of a patient sample for one or more analyte.

Therefore, an analytical device may be used in a point of care environment, such as (but not limited to) blood glucose testing, coagulation testing, blood gas and electrolytes analysis, urinalysis, cardiac markers analysis, hemoglobin diagnostics, infectious disease testing, cholesterol screening or nucleic acid testing NAT. Results may be viewed directly on the POC analyzer(s) or may be sent to the point-of-care testing (POCT) system and displayed in a Laboratory Information System with central lab results, or alongside imaging results in a Hospital Information System (HIS).

The term "analytical data" as used herein can encompass any data that is descriptive of a result of a measurement of one or more patient health parameter(s) performed by a POC analyzer of the biological sample that has been analyzed. In case of calibration, the analytical data can comprise the calibration result, i.e., calibration data. In particular, the analytical data can comprise an identifier of the patient sample for which the analysis has been performed and data being descriptive of a result of the analysis, such as measurement data.

The term "Point of Care (POC)" or "Point of Care environment" as used herein can be defined to mean a location on or near a site of patient care where medical or medically related services such as medical testing and/or treatment can be provided, including but not limited to hospitals, emergency departments, intensive care units, primary care setting, medical centers, patient homes, a physician's office, a pharmacy or a site of an emergency.

The term "point of care testing" POCT as used herein can encompass analysis of one or more patient sample(s) in a point of care environment. POCT can often be accomplished through the use of transportable, portable, and handheld instruments, but small bench analytical devices or fixed analytical devices can also be used when a handheld device is not available-the goal being to collect the patient sample and obtain the analytical data in a (relatively) short period of time at or (relatively) near the location of the patient.

POCT is performed using various POC analytical devices such as (but not limited to) analyzers for glucose, coagulation, blood gas, urinalysis, cardiac and molecular testing. Results may be viewed directly on the POC analyzer(s) or may be sent to the POCT system and displayed in a Laboratory Information System (LIS) with central lab results, or alongside imaging results in a Hospital Information System (HIS).

The term "portable computing device" can encompass any electronic appliance that can be moved easily from one location to another, in particular any handheld battery powered mobile appliance, including but not limited to a cellular telephone, a satellite telephone, a pager, a personal digital assistant ("PDA"), a smartphone, a navigation device, a smart book or reader, a combination of the aforementioned devices, a tablet computer or a laptop computer.

The term "point of care device management system" (POC-DMS) as used herein can denote a data processor configured to communicate with and manage or more POC devices via a computer network to enable a POC coordinator to manage the POC devices, or to enable maintenance personnel to monitor the equipment. Optionally, the POC-DMS can be a terminal computer connected to the same network that the POC devices can be connected to. Optionally, the POC-DMS may be provided as a server, virtual machine or a virtualized server hosted remotely to the network that the POC devices can be connected to, enabling remote management of the POC devices. It may not essential that the POC devices (analytical devices) are connected to the same subnet, or network branch, for example, as the POC-DMS.

An "analytical device" can generate many data messages (analytical device status data) in normal operation and when it is suffering from a fault condition. The messages may be displayed to a user by a display on the analytical device, or transmitted to a point of care management system (POC-DMS) attached to, or remote from, the network that the analytical device is connected to. A skilled person will appreciate that modern automatic analytical devices generate a wide range of messages.

Some message types can define messages containing assay results of tests performed on the analytical device. Other messages can contain feedback about the condition of the analytical device, such as: hardware heartbeats, specific hardware faults such as messages reporting motor overheating or a lid jam, networking information (such as LDAP or DHCP lookup messages), reagent information, temperature information, incremental counts of the number of assays performed, battery levels, software or firmware update requests, user logon information, audit log messages, security certificate messages, memory capacity information, and the like.

The term "context" in relation to an analytical device can refer to a collection of observations that may be made by or about an analytical device in a situation, location, and/or in operation conditions that can distinguish between different uses of the analytical device. "Contexts" can represent categorizable technical concepts concerning the use environment of an analytical device. The presence of a context may be detected, or iterated from, based on input stimuli detected by sensors of the analytical device, or by the fusion of contextual information such as network address.

Furthermore, example categories of technical concepts that can represent contexts may be use of an analytical device in a "teaching lab", "maintenance department", and "accident and emergency department".

The technical input stimuli derived from an analytical device sensor may be used as inputs to a range of logical rules. The rules can enable an inference of which context the analytical device can be operating in. A simple example of a context change may be taking an analytical device from a room with an acceptable temperature into a room that is too cold for an assay to be performed reliably. The context change may be inferred because an electronic thermometer included in the analytical device may report the temperature of the analytical device over time. Alternatively, the movement of the analytical device to the "maintenance department" may result in the broadcast, from the analytical device, of a plurality of unusual messages relating to the dismantling of the analytical device, such as hardware interlock signals.

The fusion of data from more than one input stimulus can enable a more accurate determination of the context. For example, by only monitoring the temperature of the analytical device, it may not be possible to determine whether or not the analytical device has moved room, or whether the temperature of same room has changed. However, information from external databases, such as a network address database or a wireless network registry may enable more accurate tracking of an analytical device around rooms in a hospital. The offline fusion of information from a user database with sensor data from the analytical device may enable the detection of the use history of the analytical device.

The term "message type" can refer to the fact that for each analytical device, a restricted alphabet or range of messages can be transmitted from the analytical device based on the status of the analytical device. The range of messages may be defined in a messaging specification.

The term "message filter" may refer to a function mapping applied to one or more input messages. The filter can perform a "many to few mapping" based on a message transfer function. The message filter transfer function (message filter configuration) may be calculated in many different ways, such as using logical rules to identify which analytical device messages have been marked with a message priority indication by a user. Messages with a message priority indication higher than a given threshold may pass through the message filter, and messages with a progressive priority indication lower than a given threshold may not pass through the message filter. Many different types of "message filter" that provide a "many to few mapping" of analytical device messages based on previously selected message priorities can be provided.

The term "message priority indication" can refer to a measure of relevance assigned to an item of analytical device status data output by, for example, an analytical device, but may not be so limited and any message present on a communication network may be assigned a message priority indication. In this application, the term "message priority indication" may at least refer to whether, or not, a message should be displayed to a user of a POC-DMS. For example, a plurality of repetitive hardware heartbeat messages emitted from each analytical device and a large plurality of analytical devices once every 10 seconds may not need to be displayed to a clinical user of a POC-DMS, because the clinical user of the POC-DMS may have more interest in messages announcing a test result.

The "message priority indication" may be assigned in many different ways and according to many different logical rules to be discussed further in this application. In one example, a user of a POC-DMS may mark an item of analytical device status data displayed in the GUI of the POC-DMS as "unimportant", with such an action representing the logical condition that the analytical device status data that so marked has a low priority. If the user does not mark the item of analytical device status data displayed in the GUI of the POC-DMS as "unimportant", the lack of action can represent the logical condition that the analytical device status data left unmarked has a high priority.

Of course, the foregoing is only one scheme of many for assigning priority to an item of analytical device status data. The present application, priority may be assigned to an item of analytical device status data not only at the POC-DMS, but also at one or more analytical devices. Modern analytical devices often have a screen, menu, and capability to view outgoing messages, for example. A user may assign priority to an item of analytical device status data based on historical records of analytical device status data (in other words, the user may label a historical dataset of analytical device status data).

An example, the POC-DMS and/or an analytical device may execute a daemon during operation that can monitor how a user views analytical device status data displayed on a display of POC-DMS and/or an analytical device. Messages that may not be actively viewed by a user after a certain elapsed time may be classified, by the daemon, as "unimportant", for example.

Furthermore, skilled person can realize that the allocation of a binary "unimportant" or "important" classification for analytical device status data can be arbitrary and many other priority allocation schemes can be used with the analytical device status data without departure from the description herein. In particular, the priority of the messages may be classified according to a discrete numerical scheme, or a continuous numerical scheme to enable thresholding, for example.

The term "communication network" as used herein can encompass any type of wired or wireless network, including but not limited to a WIFI, GSM, UMTS or other wireless digital network or a wired network, such as Ethernet or the like. For example, the communication network may include a combination of wired and wireless networks. Analytical device status data may be transmitted over the communication network.

The term "server" can encompass any physical machine or virtual machine having a physical or virtual processor, capable of accepting requests from and giving responses accordingly. It can be clear to a person of ordinary skill in the art of computer programming that the term machine may refer to a physical hardware itself, or to a virtual machine such as a JAVA Virtual Machine (JVM), or even to separate virtual machines running different Operating Systems on the same physical machine and sharing that machine's computing resources. Servers can run on any computer including dedicated computers, which individually can also be often referred to as "the server" or shared resources such as virtual servers. In many cases, a computer can provide several services and have several servers running. Therefore, the term server can encompass any computerized device that can share a resource to one or more client processes. The server can receive, process, and transmit analytical device status data.

The term "server interface" can encompass any hardware-, firmware-and/or software-based module operable to execute program logic to allow communication with an external entity (such as a server or another interface).

The term "data processing agent" can refer to a computer implemented software module executing on one or more computing devices, such as a server, that can be able to receive analytical device status data from a point of care device, and annotation data from a user or operator, and associate the analytical device status data and the annotation data. The "data processing agent" may be implemented on a single server, or multiple servers, and/or an internet-based "cloud" processing service such as Amazon AWS (TM) or Microsoft Azure (TM). The "data processing agent", or a portion of it, may be hosted on a virtual machine. The data processing agent can receive, process, and transmit analytical device status data.

The term "user interface" can encompass any suitable piece of software and/or hardware for interactions between an operator and a machine, including but not limited to a graphical user interface (GUI) for receiving as input a command from an operator and also to provide feedback and convey information thereto. In addition, a system/device may expose several user interfaces to serve different kinds of users/operators. The user interface may display items analytical device status data.

In the field of bedside testing or point of care testing, the testing can typically be performed by nurses, medical staff or doctors but also pharmacists who are collectively called "operator(s)" herein. However, anyone who possesses the required certification may be an operator. A point of care coordinator (POCC) may be at the same time an operator of POC analyzer(s) and also an operator of POC analyzer(s) may be at the same time a point of care coordinator POCC and thus user of portable computing device(s).

The application therefore generally discusses a system that can allow a user to mark messages from analytical devices as being, for example, "unimportant" in the POC IT data management system (DMS). This can also remove cluttered messages from the device message logs, because consequent messages of the same type can be obscured from a user, at least for a given amount of time.

Configurations of messages marked as "unimportant" and "important" can be shared, collected, and stored. Furthermore, such message filtering configurations can be generated for given geographical locations, network locations, user logon credentials, and technical contexts.

Furthermore, a user may download a default message filter, or a combined message filter from existing POC-DMS systems when a new device is introduced into operation. These settings may be based on collected and on the settings from users in other hospitals, for example. Therefore, the system may learn from system users as to whether a given type of message is being marked as "important" or "unimportant" in a given context worldwide, or by country, for example. From the collective notification preferences of the users in a certain context, the most usual configuration for the automated notifications can be installed.

As an example, the categorization of the analytical device data in such a way can enable display software to store more relevant analytical device data in short term memory, such as RAM, and to store less relevant analytical device data in non-volatile memory, such as a hard drive or solid-state memory. The more relevant analytical device data may then be displayed by a GUI with reduced latency and a reduced working memory requirement.

Point of Care (POC) analyzers (also known as analytical devices of medical samples) can be commonly managed by a server, and, in particular, a hardware management server, also called Point of Care Data Management System (POC-DMS). Such a server can provide connectivity for POC analyzers and management of test results, operators, quality controls, and analyzers. For example, one POC-DMS can manage all POC analyzers in a hospital, hospital department, or medical testing center.

Management of POC systems can be challenging-there can be dozens of sites, hundreds of POCT devices/kits, and thousands of operators to manage to assure quality of testing. One challenge in developing a strategy to manage POCT data concerns, how a networked POC system handles the large amount of feedback data generated by the analytical devices in an unobtrusive way to the POC team. The POC team can usually hold the responsibility for determining the test menu, selecting technologies, establishing policies and procedures, ensuring training and regulatory compliance, and providing advisory assistance to the end operators of POC technologies.

POC analyzers can send a large amount of data comprised of regular device messages (analytical device data) to a system for analytical device management (POC-DMS). The device messages can enable the analytical device to inform users about device usage, system warnings, system events, errors, or other events relating to the technical condition of one or more POC analyzers. Automatic management of the large amount of data produced, and automatically determining the technical relevance of the data, can be challenging.

FIG. 1 schematically illustrates a networked system 10 for analytical device management. The networked system 10 for analytical device management can comprise a first network 10A. The first network 10A may be divided into one or more Local Area Networks (LANs) or Wide Area Networks (WANs) corresponding to a first location 18A housing analytical devices and a second location 19A housing analytical devices. For example, first location 18A may represent a local clinic, and second location 19A may represent a general hospital. The number of locations in the first network 10A of the networked system 10 may not be essential to the functioning of the system.

The system can comprise one or more analytical devices (point of care (POC) devices) P1A to P7A, optionally a portable computing device 26A (such as a smartphone), and a server 12A communicatively connected by a communication network 16. The server 12A may, in an example, host a data processing agent 23 according to the first embodiment. In other examples, the data processing agent may be a hosted by a cloud computing service distributed over a plurality of servers and computing devices. In particular, the communication network 21 can be configured to communicatively connect the one or more analytical devices P1A to P7B.

The communication network 21 may, for example, comprise one or more of a local area network LAN provided over, for example, an Ethernet network, a Wi-Fi network, and/or a wide area network WAN such as the Internet. The communications network may comprise a Mobile Telecommunications network such as a 3G, 4G, or 5G system 28, and/or a hospital PACS network.

Optionally, the communication network 16 may connect the server 12 directly to the analytical devices (POC devices) P1A to P7B (not illustrated).

Optionally, the communication network 21 can interface with an internal communications system 22A of a health facility 18A. The internal communications system 22A may be considered an intranet, for example. A firewall and other security measures known to a person skilled in the art may be placed in between the internal communications system 22A and the communications network 21 to ensure security and confidentiality. The analytical devices P1A to P7A may communicate with a data processing agent 23 hosted on a server 40, for example, by communicating via the internal communications system 22 and the communication network 16.

The analytical devices P1A to P7A can be provided and configured for analyzing one or more patient samples in order to measure one or more patient health parameters. According to disclosed embodiments, analytical devices P1A to P7A may include transportable, portable, and hand-held instruments, but also small bench analyzers or fixed equipment 14.

For example, the tests performed by the analytical devices may include (but not be limited to) blood glucose testing, coagulation testing, blood gas and electrolyte analysis, urine analysis, cardiac marker analysis, haemoglobin analysis, infectious disease testing, cholesterol screening or nucleic acid testing. Several functional and/or operational aspects of the analytical devices P1A to P7A can be configurable or customizable using one or more analyzer parameters.

The analyzers P1A to P7A can be located in the first location 18A (corresponding to a local clinic), for example. The fixed equipment 14 may be located in second location 19A (corresponding to a general hospital, for example).

In order to identify a particular analytical device P1A to P7A, each analytical device can be provided with an analyzer identifier code, in particular, in the form of an identifier tag such as a barcode and/or an RFID tag or a serial number. Optionally, such identifiers may be associated with an entry in a database of the system for analytical device management.

The analyzers P1A to P7A can be, for example, configured to transmit analytical device status data (event messages) from the analyzers to the server 12 over the communications network 16.

The networked system 10 for analytical device management further can comprise a Point of Care Data Management System (POC-DMS), hosted, for example, on server 12A. The purpose of the POC-DMS can be to monitor and control one or more analytical devices P1A-P7A in a defined area, or network branch. For example, a POC administrator personnel can use the POC-DMS hosted on server 12A to track the condition of one or more of the analytical devices P1A-P7A, to monitor consumable usage, and a wide variety of other management activities.

One problem can be that a large number of analytical devices P1A-P7A connected to a network 10A can generate thousands or tens of thousands of analyzer data messages per hour reflecting the internal condition of the analytical devices P1A-P7A many or all of which are displayed to a POC administrator. When displayed together on a graphical user interface (GUI) of the POC-DMS server 12A, for example, it can be difficult to ascertain the condition of an individual analytical device P1A quickly enough. This can lead to latency when browsing the messages in the GUI.

Furthermore, the POC-DMS server may be accessible by a remote device over a restricted bandwidth connection such as a smartphone 26A. Attempting to display all of the thousands or tens of thousands of analyzer data messages reflecting the internal condition of the analytical devices P1A-P7A on the GUI of a smartphone POC-DMS management application may lead to unacceptable data communication latency owing to the large amount of data to be transferred.

The networked system 10 for analytical device management can also comprise a further network 10B that is illustrated in FIG. 1 as substantially the mirror image of network 10A. The further network 10B can represent a network of analytical devices run at a different hospital site, or in a different country, or hospital department as compared to the first network 10B. The description of the individual components provided above in respect of the network 10A can also apply to the illustrated components of the further network 10A for reasons of brevity. A skilled person can appreciate that a further network 10B may have a significantly different architecture to that illustrated.

In particular, the second POC-DMS 12B can also encounter problems of how to process and/or display a large number of analytical device message data output from the analytical devices P1B-P7B.

Figure 2:
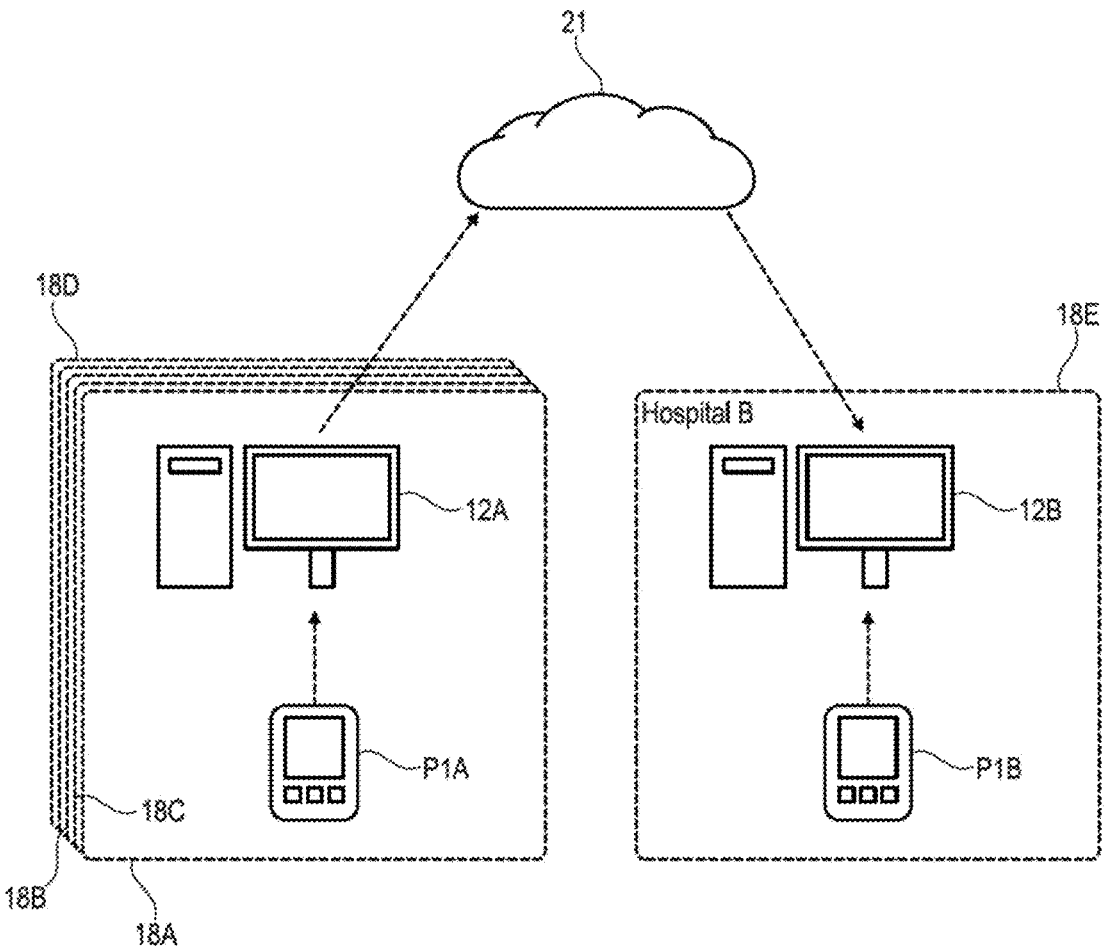
FIG. 2 illustrates schematically messaging flow in a system for analytical device management according to an embodiment of the present disclosure.

FIG. 2 schematically illustrates messaging flow in a system for analytical device management. A first network 18A comprising an analytical device P1A (such as an analytical device) and a point-of-care device management system (POC-DMS) 12A can be connected to the POC-DMS 12A via communications link 21 such as the Internet. Optionally, further networks 18B, 18C, 18D . . . can be connected via communications link 21. Analytical devices such as P1A in the first network 18A can generate a large number of status messages per hour. Conventionally, all of these can be displayed at the graphical user interface (GUI) of the point-of-care device management system (POC-DMS) 12A, and it becomes difficult to determine which messages should not be displayed.

A further network 18E that is also communicatively coupled via network 21 may contain a similar selection of analytical devices (such as P1B) and can also suffer from the problem that selecting messages for display at the graphical user interface of the graphical user interface of the point-of-care device management system (POC-DMS) 12B can be difficult. Accordingly, such systems may be further improved.

Figure 3:
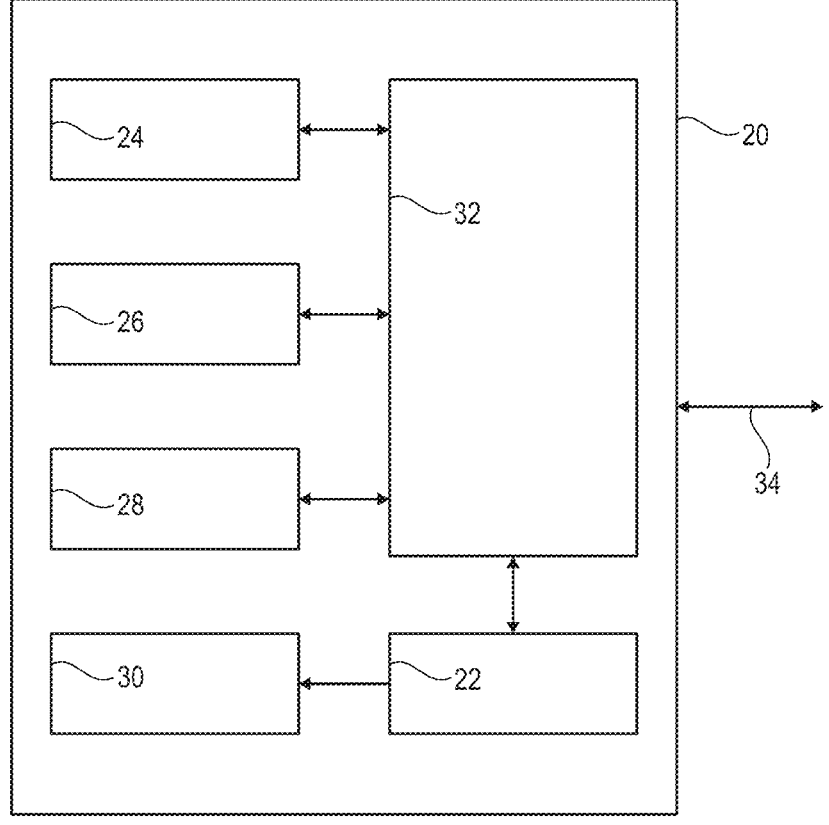
FIG. 3 illustrates schematically an example of a Point of Care (POC) device according to an embodiment of the present disclosure.

FIG. 3 schematically illustrates an example of a Point of Care (POC) device according to one embodiment.

The illustrated example of an analytical device 20 can comprise a power supply 22 configured to provide power to the analytical device 20. The power supply 22 may be, for example, a lithium ion battery or a mains power supply enabling the analytical device 20 to be portable. The power supply 22 can provide electrical energy to the other elements of the analytical device 20. The other elements can comprise, for example: a sensor device 24, an electromechanical subassembly 26, a specimen processing section 28, and an analysis unit 30. A control and communication subsystem 32 can interface with the previously listed modules. A communications link 34 can enable data transfer to and from the analytical device 20.

The sensor device 24 may, for example, comprise a photometer for measuring optical transfer characteristics through a fluid sample, although many other types of sensor can be used dependent on the application of the analytical device 20.

The electromechanical subassembly 26 can be configured to receive sample ampoules or cassettes and to load them into a specimen processing section 28 so that they can be analyzed by the sensor device 24. Following analysis, the electromechanical subassembly 26 may eject the sample ampoules or cassettes.

The specimen processing section 28 may perform pre-analysis functions such as agitation or heating of the sample to a required analysis temperature.

The analysis unit 30 may receive data from the sensor device 24 comprising a characterization of a specimen contained in the specimen processing section 28. The analysis unit 30 may perform one or more data processing operations on the data from the sensor device 24. For example, the analysis unit 30 may ensure that the result from the sensor device 24 is within expected boundaries.

Following analysis, the analysis unit 30 may transmit data from the sensor device 24 via the communications and control unit 32 to the system for analytical device management via the communications network 21, and eventually to a data processing agent 23 hosted on, for example, a server.

A skilled person can appreciate that the description of a generic analytical device 40 is provided for illustrative purposes, and that practical analytical devices may comprise fewer or more modules and functionalities.

One or more analytical devices P1A-P7A in the network can generate a wide range analytical device status data and transmit the data over the communications network 21 to a data processing agent 23. One or more modules of the analytical devices P1A-P7A may be configured to generate different types of analytical device status data (for example, event data, results data, calibration data, and maintenance-related data).

For example, the power supply 22 may generate the analytical device status data "batt_lo_10%" to indicate that the power supply 22 only has 10% of its capacity remaining.

For example, the power supply 22 may generate the analytical device status data "batt shutdown" to indicate that the power supply 22 only has shut down the battery owing to a battery fault, or having run out of battery power.

For example, the electromechanical subassembly 26 may generate the analytical device status data "motor_PCB_HB" as a repetitive "heartbeat signal" indicating that it is continuously functional.

For example, the sensor device 24 may generate a photometer printed circuit board "heartbeat" signal. In addition, the sensor device 24 may generate the analytical device status data "photometer_clean_warn" indicating that the on-board LED and/or laser requires cleaning.

For example, the specimen processing section 28 may report the analytical device status data "door_jam" to signal that a sample-handling door of the analytical device has not closed to contain the sample securely.

For example, the control and communications unit 32 may generate analytical device status data in the form of a "temp_hi_90%" signal indicating that the operating temperature of the analytical device is approaching an unsafe temperature at which inaccurate results may be provided. For example, the control and communications unit 32 may generate analytical device status data in the form of a "temp_auto_shutdown" signal indicating that the analytical device 20 has been switched off owing to an excessive temperature.

The control and communication unit 32 may also transmit analytical device status data as sequence of analysis states ("scan_barcode", "report_barcode", "assay_loaded", "test_result") to enable status of individual tests to be tracked.

The control and communication unit 32 may provide analytical device status data reporting on software configuration aspects of the analytical device 20 such as the state of internal memory, a current software or firmware version, and security parameters such as the success or failure of passwords, and networking aspects such as reporting network configuration settings, the network or MAC address of the analytical device, and optionally network uptime and downtime.

Optionally, the analytical device status data can be time stamped by the control and communication unit 32 to an accuracy of about 10 seconds, about one second, about 0.1 s, about 0.01 s, or an even higher accuracy as enabled by, for example, the ethernet time protocol or network time protocol. This can enable a data processing agent 23 hosted by a remote server to reconstruct the sequence of received analytical device status data relative to the time that an event occurred triggering the generation of the analytical device status data.

Of course, the control and communication unit 32 may generate more complicated analytical device status data comprising concatenated groups of individual event messages based on rules contained in the control and communications unit 32 of the analytical device 20.

Optionally, the analytical device status data may be concatenated with test result data obtained from the analysis of a patient sample.

The analytical device status data can be transmitted as a data packet encapsulated according to the communication system 16A used in the system for analytical device management, as known by persons skilled in the art. The data packet can comprise the analytical device status data, and may comprise any necessary arrangement of header information to enable reliable routing of the analytical device status data to the data processing agent. The data packet may comprise only one bit of payload information (for example, in the case of a heartbeat flag). Alternatively, the data packet may comprise a large amount of information (for example, several kilobytes or megabytes). The control and communications unit 32 of the analytical device 20 may be configured to buffer a plurality of analytical device status data messages for a given amount of time, and to concatenate the messages into one data packet, for example. This may lead to longer battery life of a handheld analytical device.

A skilled person can appreciate that the foregoing description of an analytical device 20 also applies to the analytical devices P1B-P7B communicatively coupled to the further communications network 10B.

Figure 4:
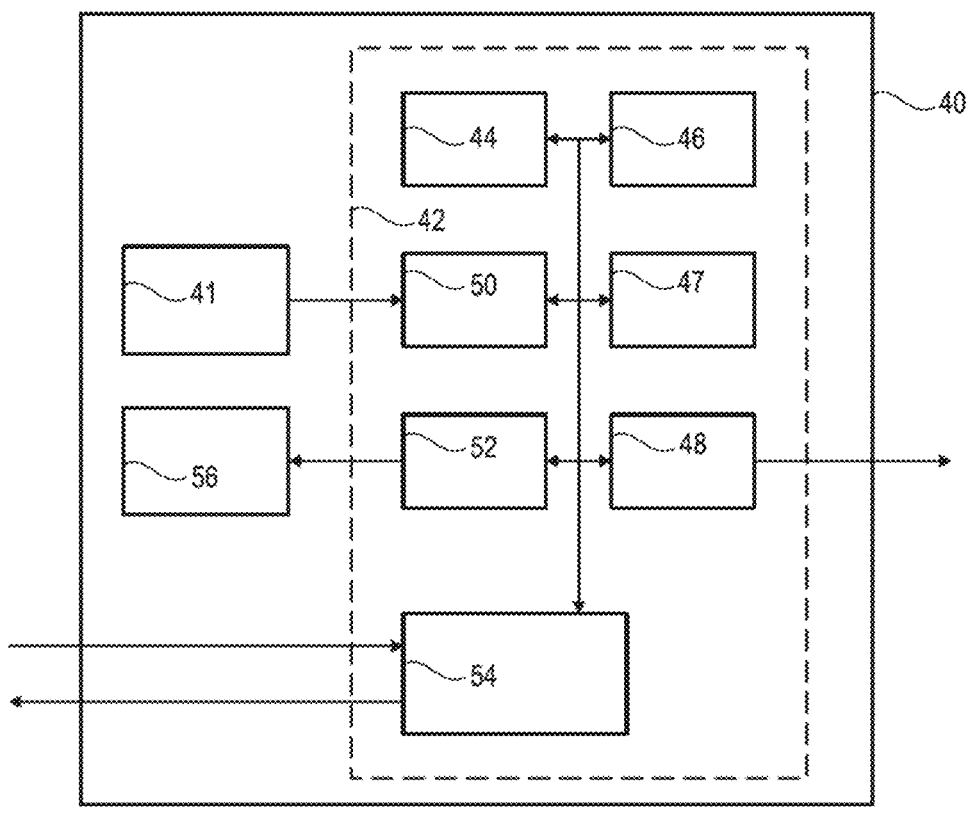
FIG. 4 illustrates schematically an example of a server configured to host a data processing agent according to an embodiment of the present disclosure.

FIG. 4 schematically illustrates an example of a server 40 configured to host a data processing agent according to an aspect.

In this example, the server 40 can comprise a motherboard 42 comprising a random access memory (RAM) 44, a read-only memory (ROM) 46, a central processing unit (CPU) 47, an input/output interface 48, a data storage interface 50 (such as an interface to a non-volatile memory 49), a display interface 52, and a communication interface 54, however a skilled person can appreciate that many different types of server configuration can be provided with more or fewer modules having other functionality.

The central processing unit 47 of the server 40 can be configured to obtain, from an interfaced non-volatile memory 49 (for example), computer readable instructions which, when executed, instantiate a data processing agent for generating a message filter configuration in the random access memory 44 of the server 40.

The communication interface 54 of the server can be configured to interface with the communications network 21. Analytical device status data from an analytical device P1A to P7A can be received at the server 40 via the communication interface 54 of the server.

Optionally, the analytical device status data can be provided directly to the random access memory 54 by processing and analysis by the central processing unit 47. Optionally, the analytical device status data can be written to the non-volatile memory 49 for subsequent analysis.

Optionally, the analytical device status data may be written (cached) to an external file store (not shown). On demand by the central processing unit 47, a request for the analytical device status data may be sent to an external file store over the communications network 21. The external file store may, pending authentication and authorization, transmit the analytical device status data to the server 40, where it may be subsequent processed and combined with annotation data.

The benefit of the foregoing optional embodiment can be that a large amount of analytical device status data may be robustly stored until it needs to be processed. It may not be essential that the message filter configuration at the same time that the message priority indication is received, and/or as the analytical device status data is performed as data is received. Alternatively, the two types of data may be associated in a post-processing step using, for example, timestamp data.

Optionally, the message filter configuration can be updated or generated immediately when a message priority indication is received by the data processing agent.

The data processing agent 23 can be instantiated on the server 40 from machine-readable instructions obtained, for example, from the random access memory 44, or the read-only memory 46, the input/output interface 48, or the data storage interface 50. The data processing agent 23 can be therefore configured to receive one or more items of analytical device status data, and/or one or more items of message priority indication data. The data processing agent 23 instantiated on the server 40 can be configured to generate a message filter configuration based on techniques to be discussed subsequently, and to transmit the message filter configuration as a data structure (signal) to one or more further point of care devices P1B-P7B communicatively coupled to a further communications network 10B.

Optionally, the server 40 hosting the data processing agent 23 can be configured to display the message priority indication data and/or the message filter configuration on a local display via a local display driver 56.

Figure 5:
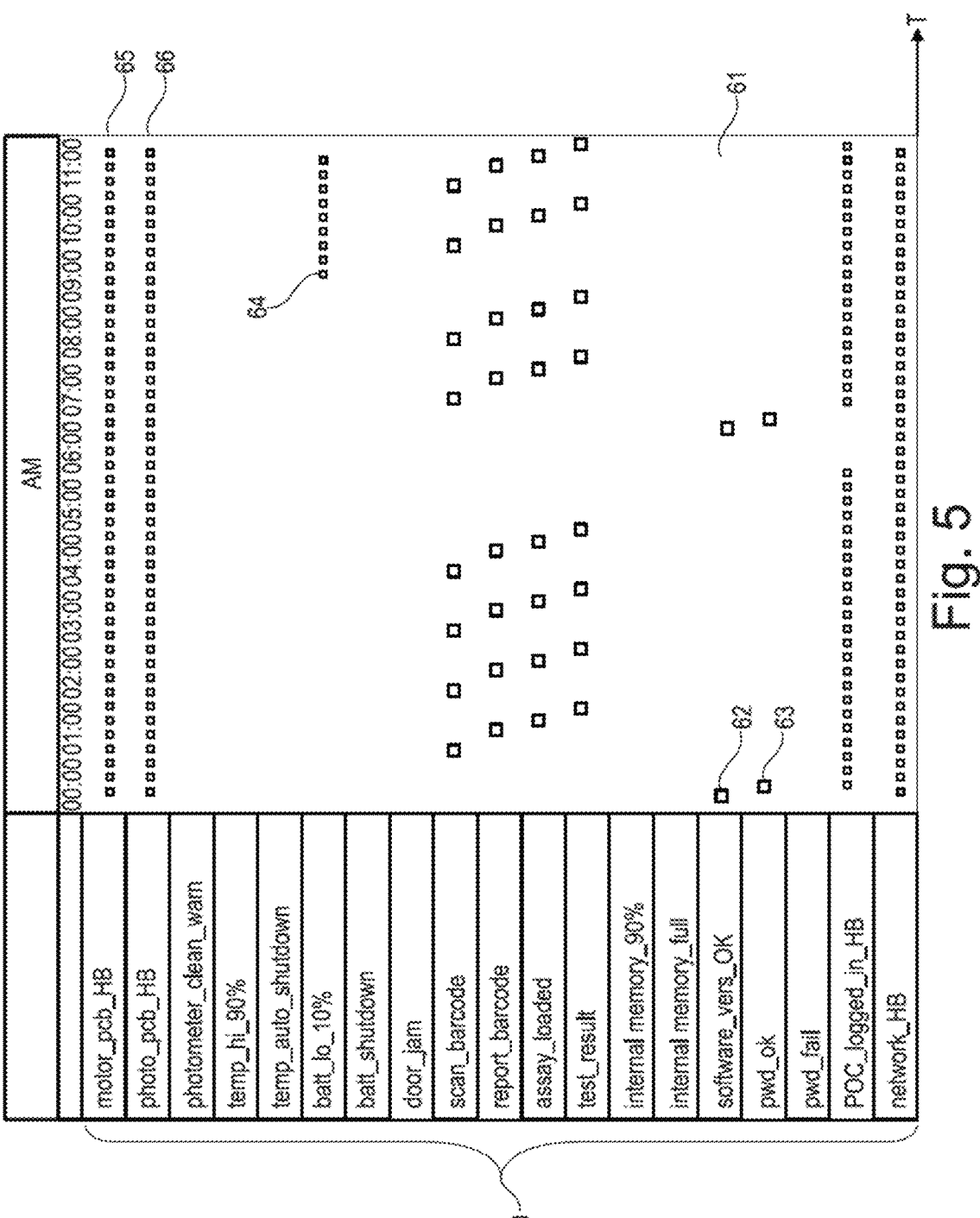
FIG. 5 illustrates schematically an example of data messages output from one point of care device in an example context according to an embodiment of the present disclosure.

FIG. 5 schematically illustrates an example of the problem caused by a continuous messaging flow of analytical device status data from automated POC analyzer P1A to POC-DMS 12A. In the illustrated scenario, analytical device P1A can transmit analyzer status data as messages selected from a message set 60. The example of FIG. 5 shows an example of the type of analytical device status data that may be received by the data processing agent 23.

The chart 62 represents the analytical device status data generated by the analytical device as it is generated in time T, with the chart 61 representing a twelve hour early morning shift. Repetitive heartbeat signal "photo_pcb_HB" can indicate that the photometer is operating reliably, but can generate a large number of messages in time. Upon initialization of the analytical device, BIOS check can ensure that the software (firmware) loaded onto the analytical device is of the correct version, indicated by event message 62 "software_vers_ok", for example.

Shortly afterwards, a user of the analytical device can log onto the device using a correct password, which can be reported to the data processing agent using a further transmission of analytical device status data "pwd_ok" 63. Over the course of the shift, a sequence of eight analysis runs can be performed, as shown by the repetitive sequence of analytical device status data reporting the scanning of a barcode, the reporting of a barcode the loading of an assay, and the provision of a test result. At around T=09:30 am, the analytical device can begin to report a low battery alarm "batt_lo_10%" 64 in the form of analytical device status data transmitted to the data processing agent 23.

Throughout the time that the automated POC analyzer P1A is operating, the "motor_pcb_HB" 65 and "photo_pcb_HB" 66 signals can be repetitively asserted by repetitively sending message data to the POC-DMS 12A. These can inform the POC-DMS 12A that the respective hardware subsystems of the POC P1A are functioning correctly. However, such message data can obscure more important messages, such as the "batt_lo_10%" 64 when displayed in a GUI of the POC-DMS 12A. Furthermore, the storage and manipulation of large numbers of "heartbeat" signals such as the "motor_pcb_HB" 65 and "photo_pcb_HB" 66 signals in the working memory (random access memory) 44 becomes cumbersome and prone to high latency, when such messages can be immediately archived in in non-volatile memory, such as a database, instead. The problem can be compounded when further devices from different manufacturers are operated on the network 10A, because the sources of analytical device message data may be unknown to POC-DMS 12A, or transmit data in an unknown or partially unknown format.

According to an embodiment, it can therefore be provided a computer implemented method for generating a message filter configuration based on a message priority indication received from a first analyzer network 10A, wherein the first analyzer network comprises at least one analytical device P1A configured to generate analytical device status data.

The method can comprise receiving, at a data processing agent 23, a message priority indication indicating a priority assigned to the analytical device status data in the first analyzer network 10A; providing, at the data processing agent 23, at least one message filter configuration 72 based on the message priority indication of the analytical device status data; and communicating the message filter configuration 72, or a portion thereof, to a second analyzer network 10B comprising a second analytical device P1B of medical samples.

According to an embodiment, it can be further provided to receive, at the data processing agent 23, a plurality of message priority indications from one or more further analyzer networks, wherein the message filter configuration 72 can be generated based on the plurality of message priority indications.

The data processing agent 23 can receive from POC-DMS 12A in a first network 10A a plurality of message priority indications assigned to analytical device status data in the first network 10A.

In an example, an operator of a user interface 24A of the POC-DMS 12A can mark the first set of messages as "unimportant" (in the sense of not needing to be displayed by the POC-DMS 12A in regular use). Implicitly, the messages left unmarked can be "important" (and may need to be displayed by the POC-DMS 12A in regular use).

For example, the management software hosted on the POC DMS 12A may comprise a user interface 24A having a selection button enabling the user to mark that a specific message is "unimportant", thus creating a message priority indication associated with the type of specific message marked "unimportant".

In an example, the message priority indication associated with the type of specific message marked "unimportant" can be immediately and directly transmitted from the POC-DMS 12A to the data processing agent 23 after the specific message can be marked as "unimportant" in the POC-DMS 12A. This can enable message importance indications to be transmitted to the data processing agent 23 for further handling with a minimum of latency.

Most conveniently, the message priority indication can be appended as a field or a flag to the analytical device status data to which it relates.

In an example, the analytical device status data can be a communication compliant with the "HL7" protocol (Health Level Seven, Ann Arbor MI, USA) and/or the ASTM protocol (for example, ASTM 1394 LIS2).

In other words, the message priority indication can be concatenated or inserted into the analytical device status data whose priority it reports. In this case, when the analytical device status data is received at the data processing agent 23, the message priority indication may be read, extracted or de-encapsulated from the analytical device status data It may not be essential that the message priority indication is concatenated or inserted into the analytical device status data, or otherwise transmitted with the analytical device status data. In an example, the message priority indication can be transmitted separately to the analytical device status data.

In an example, the POC-DMS 12A can maintain a local database of message priority indications. For each type of message received from an analytical device in the first network 10A, a record associated with the type of message in the local database of message priority indications in POC-DMS 12A can be incremented with the classification of "important" or "not important" provided by the user via the GUI of POC-DMS 12A.

In this example, the data processing agent 23 may be configured to poll the local database of message importance stored at POC-DMS 12A on a regular or an irregular basis to transfer a copy of the local database of message priority indications, or a subset of the local database of message priority indications, to the data processing agent 23 for further handling. In this way, a large database of message priority indications information can be transferred to the data processing agent 23 at a time when the network is less busy, or the data processing agent 23 can poll the POC-DMS 12A for a small proportion of information held in the local database of message priority indications.

In an example, the POC-DMS 12A may continuously, or batch-forward message priority indications over the Internet to a message storage database accessible by the data processing agent 23, to enable the data processing agent 23 to access the message priority indications at any time.

The message priority indication may be a binary indication for each type of message received at the POC-DMS 12A. However, the message priority indication may be a continuous number (for example in the range zero to five), or the message priority indication may be selected from an alphabet of message priority categories. A subset of message types may enable a different type of priority indication, dependent on the type of the message.

In high-level terms, POC-DMS 12A in the first network 10A can receive messages selected from a finite set (or alphabet) of message types. The finite set of message types can be defined by considerations such as the type of POC analyzers and other devices connected to the first network 10A and configured to communicate with the first POC-DMS 12A, the manufacturer of the devices connected to the first network 10A, the software configuration of the devices connected to the first network 10A, and the type of tests performed by the devices connected to the first network 10A. If a message can be generated by an analytical device P1A and transmitted to the first POC-DMS 12A then it can be considered to be within the finite set of message types.

The message filter applied to messages sent by the analytical devices (P1B-P7B) in the second network 10B and received at a POC-DMS 12B in the second network 10B can operate according to the message filter configuration 72. The message filter configuration 72 can be derived at least partially on the basis of message priority indications received from analytical devices P1A-P7A in the first network 10A.

The message filter configuration 72 can be a mapping between the finite set of message types (taken as an input), and a preferred sub-set of message types (message types displayed to a user at a POC-DMS 12B in the second network 10B). The preferred set of message types can be a subset of the overall set of message types. The mapping between the overall set of message types and the preferred set of message types can be provided based on the message priority indications received, for example, via a GUI of the POC-DMS at the POC-DMS 12A in the first network 10A.

A skilled person can appreciate that within the definition of the message filter configuration 72, a wide range of approaches to generate the message filter configuration 72 such that it can perform the task of displaying a subset of preferred message types out of an overall set of message types.

In an example, the message filter configuration 72 may be generated based on thresholds of message priority indications received for a single message type.

In an example, the message filter configuration 72 may be generated based on logical rules affected by a plurality of message types.

In an example, the message filter configuration 72 may be generated based on consideration of the network configuration, user information, and/or context of the origin of a given message leading to a message priority indication.

In an example, the message filter configuration 72 can be generated by the data processing agent 23 dependent on the identity of a specific user of the first POC-DMS 12A. The identity of the specific user can be obtained, for example, from logon credentials of the POC-DMS 12A. In this example, a plurality of message filter configurations 72 can be generated corresponding to the number of users of the POC-DMS 12A. When the specific user logs onto a second POC-DMS 10B based on a second network 12B, the second POC DMS 10B can be configured to request the message filter configuration 72 from the data processing agent 23 that corresponds to the identity of the specific user. In this way, a message filter configuration 72 preferred by a specific user of the POC-DMS 12A, 12B can be transferred between work locations, for example.

According to an embodiment, providing the message filter configuration can comprises identifying a type of the analytical device status data associated with the message priority indication and inserting or updating a record in a data structure defining the message filter configuration 72, wherein a value in the record can store the priority assigned to the identified type of analytical device status data; and adjusting the value held in the record based on the message priority indication 72 corresponding to the identified type of the message, to thereby provide the message filter configuration.

FIG. 6 schematically illustrates an example of generating a message filter configuration 72 based on a message priority indication of analytical device status data. For example, a count of the total number of message priority indications, along with the number of message priority indications marked "unimportant" for each type of message can be gathered in a message accumulation database 68. The message accumulation database 68 may be continuously accumulated at the data processing agent 23, stored as a local database at the POC-DMS 12A, or stored elsewhere on the Internet and polled when necessary. Qualitative inspection of message accumulation database 68 can reveal that users of the POC-DMS 12A considered the heartbeat signals ending in "HB" to be somewhat unimportant, but did not cancel any of the "test_result" messages.

In this example, a category importance ratio for each message type can be calculated with the result provided in category importance data structure 69. For each type, the category importance ratio can represent the number of messages of a given type marked "unimportant" divided by the total number of received messages of that type.

In this example, a population importance ratio for each message type can be calculated, with the result provided in population importance data structure 70. The total number of messages of any type can be accumulated. For each type of message, the number of messages marked "unimportant" can be divided by the total number of messages of any type.

An example of a message filter configuration is a data structure 72 containing, for each type of message, a binary indication of whether, or not, a given message type should be displayed when it is received at a further POC-DMS 12B in a second network 12B comprising analytical devices The message filter configuration 72 can be generated based on the message priority indications received at the POC-DMS 12A in the first network 10A.

In an example, the message filter configuration 72 can be generated based on a filter rules set 71. In FIG. 6, a first filter rule in the filter rules set 71 can define that a given type of message may be displayed if the category importance ratio is less than a given ratio (0.15).

A second filter rule in the filter rules set 71 can define that a given type of message may be displayed if two conditions are met: firstly, if the population importance ratio for the given type of message is less than a given ratio (0.1), and secondly if the message type is NOT of type "test result."

Therefore, one or more filter rules can be applied to the received message priority indications to generate the message filter configuration 72. A skilled person can appreciate that the two rules provided are examples, and that many filter rules enabling message importance discovery may be provided.

Subsequently, the data processing agent 23 can transmit the message filter configuration 72 to a POC-DMS 12B in the second network 10B. The POC-DMS 12B in the second network 10B filters and incoming set of messages received from analytical devices P1B-P7B in the second network 10B using the message filter configuration 72 received from the data processing agent 23.

The message filter configuration 23 may be provided based on the message priority indication of the analytical device status data in many different ways.

Analytical device status data generated by an analytical device can be optionally timestamped. Alternatively or in addition, a message priority indication can be optionally time stamped when a user marks a type of message in a set of message types as "unimportant" using the POC-DMS 12B. Therefore, the weight that an individual message priority indication can provide to the message filter configuration 72 may be varied based upon the time that the individual message priority indication was provided, or alternatively based on the timestamp of the analytical device status data associated with the individual message priority indication.

According to an embodiment, the message filter configuration can be partially, or entirely, adjusted as a time-based function.

According to an embodiment, at least one value held in the record of the message filter configuration 72 can be adjusted based on the time of generation of the analytical device status data to which the message priority data is linked.

According to an embodiment, at least one value held in the record of the message filter configuration 72 can be adjusted based on the time of generation of the message priority data is linked to an item of analytical device status data.

For example, the message filter configuration 72 may be recalculated at the end of every year, month, week, or day, excluding message priority data generated more than a given amount of time in the past. This can ensure that the message filter configuration 72 does not diverge to a point where certain message types can never again be displayed.

According to an embodiment, it can be further provided to obtain network configuration data at least partially characterizing the network configuration of the analytical device in the first analyzer network 10A from which the message priority indication originated and to generate or update the message filter configuration based, at least partially, on the network configuration data of the first analyzer network 10A.

Turning back to the network configuration diagram of FIG. 1, the first network 10A can comprise a first branch in first medical institution (a local clinic) 18A and a second branch in a second medical institution (a general hospital) 19A. The first branch can comprise at least handheld analytical devices PSA and P6A of type "1", a handheld analytical device P4A of type "2", and several desktop analysis devices. The second branch in medical institution 19A can comprise at least handheld analytical devices P2A and P3A of type "1", and handheld analytical device P1A of type "2". Furthermore, the second branch in medical institution 19A can have a different arrangement of desktop analysis devices.

The network configuration data may be obtained, for example, by performing SNMP analysis (simple network management protocol) on the analytical device data of the first network 10A to obtain the network topology. Alternatively or in addition, the POC-DMS 12A in the first network 10A may comprise a registry data structure providing details about the network configuration of the first network 10A. This information can be discovered by reference to the MAC address of devices on the network, a manufacturer registration number held in the firmware of an analytical device, or the IP or network address of an analytical device.

An advantage of generating or updating the message filter configuration based at least partially on network configuration data can be that a given type of analytical device P1A-P7A may be known to generate an excessive number of messages of a type that do not need to be viewed at the POC-DMS 12A. The present embodiment can identify the presence of a type of POC P2A, P3A in a network 10A. Upon identification of the type of POC P2A, P3A that generates an excessive number of messages of a type that do not need to be viewed at the POC-DMS 12A, one of more entries may be added to the message filter configuration 72 capable of filtering the messages of the type that do not need to be viewed at the POC-DMS 12A. However if the presence of a type of POC P2A, P3A in a network 10A is not found, then such entries do not need to be added to the message filter configuration 72, and the entries omitted from the message filter configuration 72.

As the analytical devices P1A-P7A are moved around different departments of the hospital and used in different settings, taken for repair, used in the teaching context, or even removed from the hospital to be used by a community nurse in a sequence of patient home visits, the pattern of analytical device messages describing the internal condition of the analytical devices P1A-P7A can change.

For example, an analytical device present in a hospital may remain at an acceptable operating temperature, but an analytical device left in the car of a community nurse overnight during winter may fall below an acceptable operating temperature, and can thus trigger a stream of analytical device data comprising low temperature limit notifications. The transmission, storage, and display of such messages to a POC administrator on a POC-DMS GUI may be unnecessary, because for the purposes of this example it may be acceptable to leave a POC analyzer in a cold car overnight provided it is at an acceptable operating temperature in use.

However, in practice, it can be very difficult for a POC administrator to monitor the operation contexts of a large number of devices under their responsibility, to determine whether, or not, such a condition caused by a variation in context is problematic or not.

Such subtle or significant changes to the pattern of analytical device status data can be used to identify, for each analytical device in a set of analytical devices P1A-P7A, a context of use of each analytical device. Analytical device status data originating from distinct contexts may be assigned differing priorities by a user of the POC-DMS 12A, so that when it is identified in future that one or more of analytical devices can be used in a distinct use context, the analytical device status data may automatically be filtered according to the use context of the analyzers.

According to an embodiment, it can be further provided to identify, using a context identification engine 78, one, or more contexts of the first analyzer network 10A and/or the first analyzer management system 12A, and/or the at least one analytical device P1A from which the message priority indication originated and to provide, or update, the message filter configuration based on the identified context.

According to an embodiment, a plurality of message filter configurations can be generated corresponding to the plurality of identified contexts.

According to an embodiment, a first plurality of items of analytical device status data originating from an analytical device present in an identified first context can be assigned to a first plurality of message priority indications. A second plurality of items of analytical device status data originating from an analytical device present in an identified second context can be assigned a second plurality of message priority indications. A first message filter configuration 72 to filter subsequent analytical device status data originating from an analytical device in the identified first context can be generated using the first plurality of message priority indications. A second message filter configuration to filter subsequent analytical device status data originating from an analytical device in the identified second context can be generated using the second plurality of message priority indications.

Optionally, the first and second message filter configurations may be generated using an identical rule set, wherein the identical rule set can be applied to the first plurality of message priority indications to generate the first message filter configuration, and wherein the identical rule set can be applied to the second plurality of message priority indications to generate the second message filter configuration.

Optionally, the first message filter configuration 72a may be generated using a first rule set, wherein first rule set can be applied to the first plurality of message priority indications to generate the first message filter configuration. The second message filter configuration 72b may be generated using a second rule set, wherein the second rule set can be applied to the second plurality of message priority indications to generate the second message filter configuration, and wherein the second rule set can be different to the first rule set.

Optionally, the context identification engine 78 can comprise a first instance tracking one or more use contexts of a first analytical device.

Optionally, the context identification engine 78 can comprise a second instance tracking one or more use contexts of a second analytical device, wherein the plurality of use contexts of the first instance can be different to the use contexts of the second instance.

Optionally, the first instance 78a of the context identification engine 78 can be a first finite state machine and the second instance 78b of the context identification engine can be a second finite state machine. The first finite state machine and the second finite state machine can comprise an identical arrangement of states and/or state transitions. The first and second finite state machines can receive input stimuli from at least one of the POC management system (POC-DMS), and/or one or more of the analytical devices P1A-P7A.

Optionally, the first instance 78a of the context identification engine 78 can be a first finite state machine and the second instance 78b of the context identification engine 78 can be a second finite state machine. The first finite state machine and the second finite state machine can comprise a different arrangement of states and/or state transitions. The first and second finite state machines can receive input stimuli from at least one of the POC management system (POC-DMS), and/or one or more of the analytical devices P1A-P7A.

As noted, in an example, the message filter configuration 72 may be generated based on consideration of the use context of the analytical device P1A-P7A that can generate an item of analytical device status data (message) connected to an associated message priority indication.

The use context of the analytical device P1A may be inferred based on many different input stimuli, as will subsequently be discussed.

In an example use case, a first context can be that of a POC-DMS 12A and associated analytical devices P1A-P7A can be located in an accident and emergency ward. In an accident and emergency ward, a large number of portable analytical devices P1A-P7A can be carried between cubicles and be reliant mainly on battery power, although they may perform a slightly lower than average number of tests. Data communication can be via, for example, wireless networking such as secured Wi-Fi. Machine accidents such as dropping an analytical device P1A on the floor, or even misplacing an analytical device P1A in a store cupboard, may be more prevalent in a busy accident and emergency ward. Accordingly, analytical devices P1A-P7A in the accident and emergency context may report more "low battery" messages, data communication, accelerometer shock messages, or wireless communication configuration messages than average. Some of these may become repetitive and used to associate POC-DMS 12A in an accident and emergency department context.

For example, a second context can be that of a POC-DMS 12A and associated analytical devices P1A-P7A located in a pathology laboratory. In this case, high throughput use of the analytical devices P1A-P7A may mean that quality control reminders, ingredient or reagent fill level reminders and a large number of tests per hour compared to other contexts, and the like can be more prevalent than average at an associated POC-DMS 12A located in a pathology laboratory.

For example, a third context can be that of a POC-DMS 12A and associated analytical devices P1A-P7A located in a teaching environment. Modern analytical devices P1A-P7A can generate a large number of messages, but some of these may be distracting in a teaching or training environment, especially when the results are not being used in "live" medical cases. Accordingly, a user of associated POC-DMS 12A in a teaching or training environment may prefer to enhance importance of basic test result messages, and to de-emphasize the importance of repetitive hardware monitoring messages, for example.

Each of these example contexts can have particular characteristics that can lead to a technically distinctive difference in the flow of messages that reach the POC-DMS 12A in each context. The difference in messages may result from qualitative differences between use contexts. Accordingly, message filtering can be adjusted based on the context that analytical devices P1A-P7A are used in. This can be particularly advantageous when portable analytical devices P1A-P7A are translated between contexts in quick succession (such as an analytical device being moved from a teaching environment to the accident and emergency environment).

The context identification engine may use a wide range of information available from at least one of the network 10A, the POC-DMS 12A, or the analytical devices P1A-P7A to infer or to discover context in which a given analytical device P1A-P7A is operating. Generating different message filter configurations 72 to filter messages from analytical devices P1A-P7A in different contexts can mean that messages that are irrelevant when an analytical device is present in a first context, but relevant when an analytical device is in a second context, can be displayed automatically and without user intervention at, for example, the POC-DMS 12B of a second network 10B that has received the plurality of message filter configurations 72 generated by the data processing agent 23.

Figure 7:
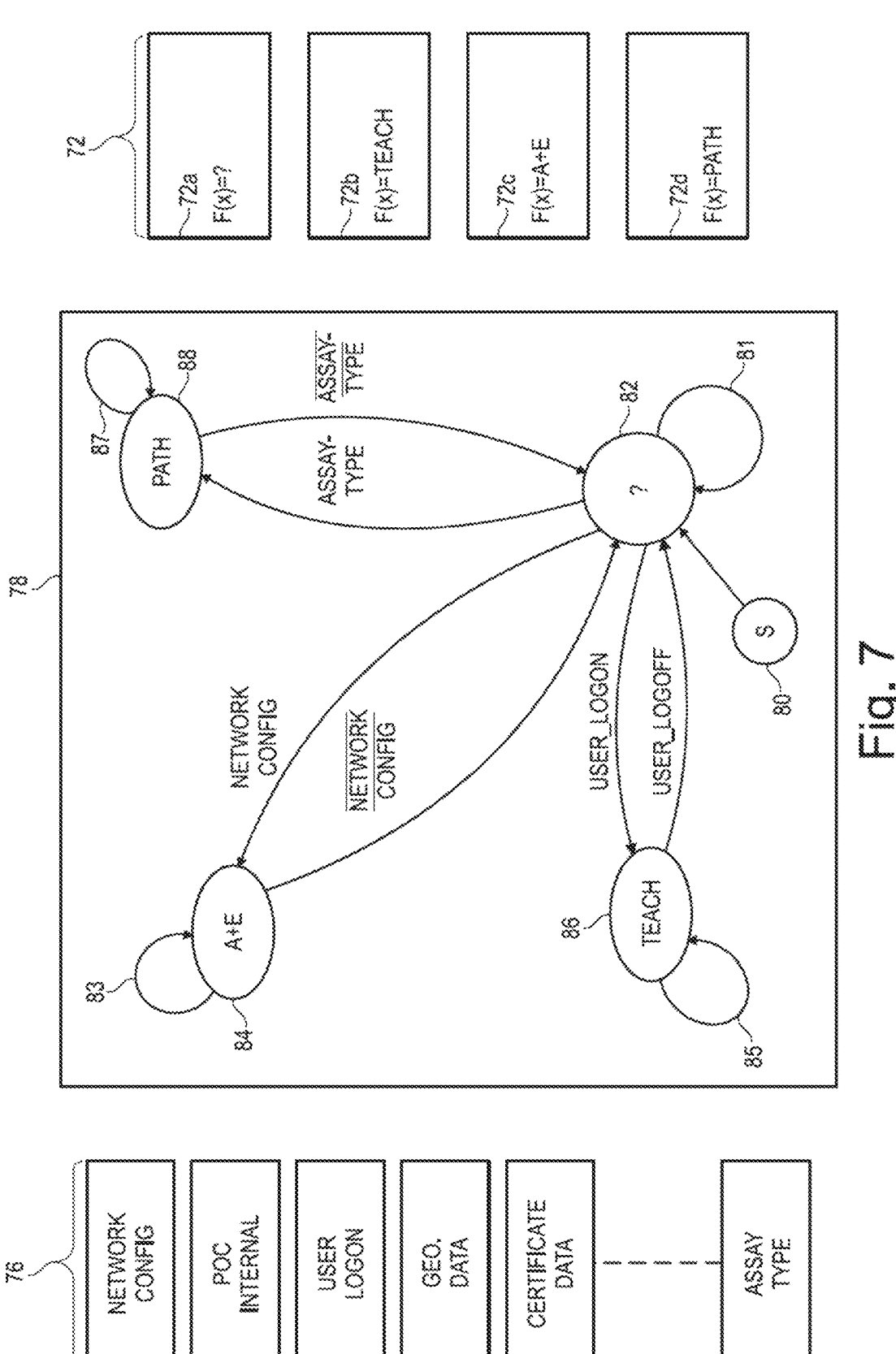
FIG. 7 illustrates schematically an example of instance of a context identification engine capable of tracking the context of a single analytical device according to an embodiment of the present disclosure.

FIG. 7 illustrates a unique instance of the state machine 78 that models the context of an individual analytical device P1A.

Based on the foregoing discussion of potential use cases, the state machine may have an "accident and emergency", "pathology laboratory", and "teaching environment" state along with a "undetermined state"

In the example of FIG. 7, the assignment of states to contexts, the mapping of state transitions between states, and the selection of input stimuli (signals) or combinations of input stimuli defining transitions between states is provided as an illustrative example. A skilled person can appreciate that many more, or fewer, states may be provided based on the number of contexts that are intended to be tracked. The state transitions between states may be provided in many different ways. The input stimuli defining transitions between such states may be obtained from a variety of different sources available to the data processing agent 23.

The state machine 78 in the context identification engine can comprise a starting edge 80 directed to the indeterminate state 82. In the absence of conditions indicating that the state should change to "teach" 86, "A&E" 84, or "PATH" 88, the state machine can dwell around the indeterminate state 81, indicating that the context cannot presently be determined. In this case, the message filter configuration 72 can be output as a default message filter configuration applicable to many different contexts.

Optionally, when the context identification engine identifies that an analytical device P1A is in an indeterminate context, all records in the message filter configuration 72a for all types of message can be set to unity to ensure that all messages can be forwarded from the data processing agent.

The data processing agent 23 may detect a user logging on to an analytical device P1A with a status of "student". The state machine can exit the "indeterminate" state and enter the "teach" state 86. The state machine can remain in the "teach" state 86 until POC-DMS 10A detects a user logging off the analytical device P1A, in which case the state machine re-enters the "indeterminate" state.

When the context identification engine identifies that an analytical device P1A is in the "teach" state, records related to message types in the message filter configuration 72 may be set to ensure that analyzer status data irrelevant to a teaching assignment are not displayed to the student via the GUI of an analytical device P1A,B or a POC-DMS 23A,B.

In this example, starting from the indeterminate state 82, when a network configuration "NETWORK_CONFIG" of network 10A is detected matching a pre-assigned condition, the state machine can transition to the "A&E" state 83. The network configuration may change to match the condition "NETWORK_CONFIG", for example, when an analytical device P1A is used in combination with a unique arrangement of other network devices indicative of an "A&E" department. Alternatively, the network configuration may be looked up in a network configuration directory revealing that the network address (or IP address) of an analytical device matches a range of network addresses in an "A&E" department.

When the context identification engine identifies that the analytical device P1A is in the "A&E" context, message priority indications relating to analytical device data output from the analytical device P1A in the "A&E" context can be used to generate the message filter configuration 72c.

In the example of FIG. 7, when the "NETWORK_CONFIG" is not asserted, the state machine can leave the "A&E" and return to the indeterminate state 82.

In the example of FIG. 7, when the context identification engine identifies that an "ASSAY_TYPE" signal has been inserted implying that an analytical device is performing an assay that can only be performed in a pathology laboratory context, the state machine can transition into the "PATH" state 88 and remain there until the "ASSAY_TYPE" signal changes to a state defining that the analytical device is not performing the assay that can only be performed in a pathology context.

When the context identification engine identifies that the analytical device P1A is in the "PATH" context, message priority indications relating to analytical device data output from the analytical device P1A in the "PATH" context can be used to generate the message filter configuration 72d.

Figure 8:
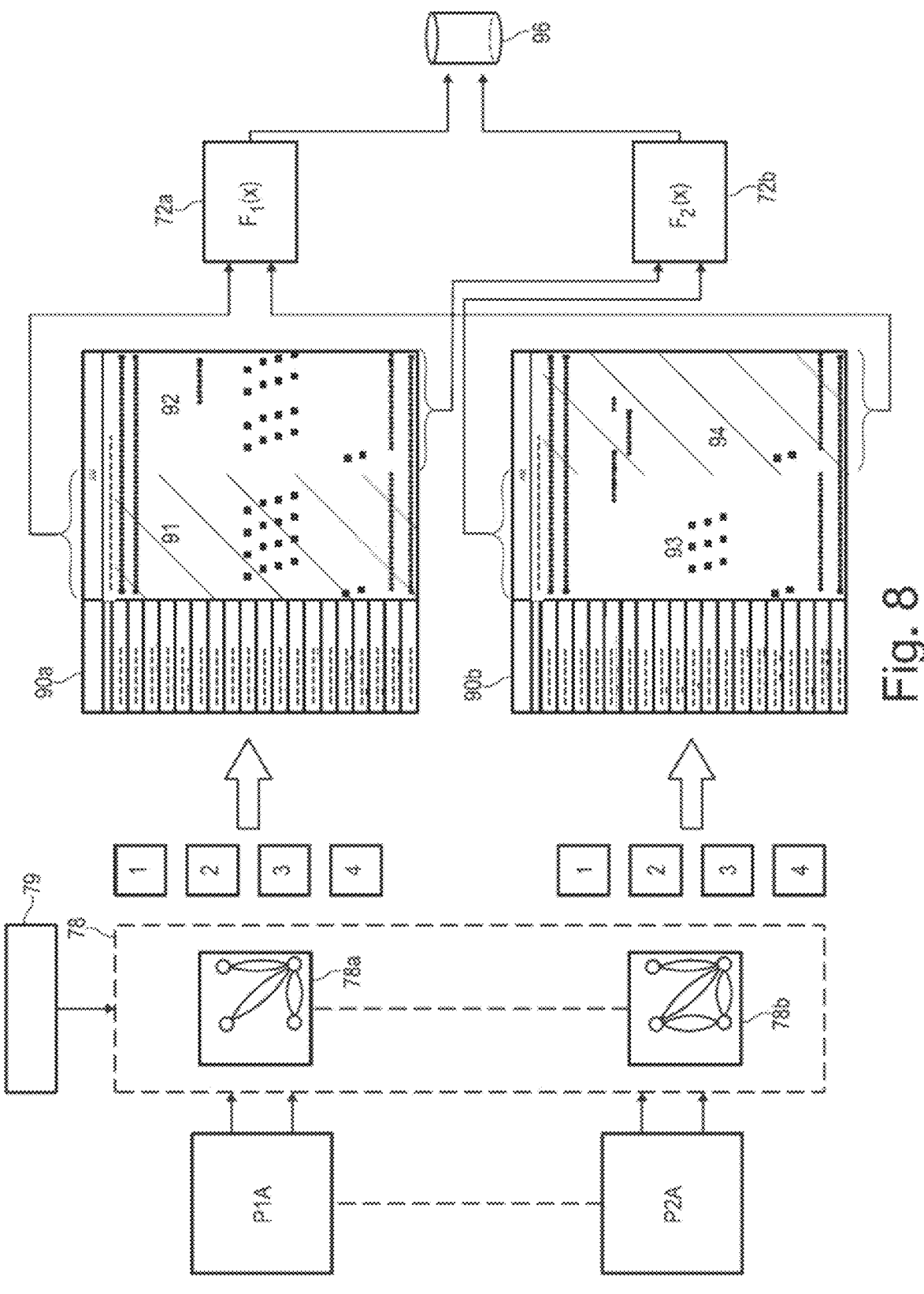
FIG. 8 illustrates schematically an example a context identification engine capable of tracking the context of a single analytical device using a plurality of instances according to an embodiment of the present disclosure.

FIG. 8 schematically illustrates an example of a context identification engine 78 maintaining a plurality of unique instances 78a, 78b for each active (switched on) analytical device (POC device) in the first network 10A comprised in a portion of a context identification engine capable of tracking the context of a single analytical device.

For example, the context identification engine 78 can track the context of analytical device P1A using the first context identification instance 78a. In this example, the context identification instance 78a may be a finite state machine as discussed above with four possible states discussed above, but a skilled person can appreciate that more or fewer states, or a different context tracking approach may be applied.

The context identification engine 78 can tracks the context of analytical device P2A using the second context identification instance 78b. In this example, the context identification instance 78b can also be a finite state machine as discussed above with four possible states discussed above, but a skilled person can appreciate that more or fewer states, or a different context tracking approach may be applied.

The context identification engine 79 can receive input signals used to infer the context of P1A and P2A, such as a network address server, from analytical device data output by P1A and P2A themselves, from a logon server, and the like.

Accordingly, message priority indications provided in respect of analytical device data output by P1A can be indexed with one out of the four available contexts currently identified by context identification instance 78*a*. Message priority indications provided in respect of analytical device data output by P1B can be indexed with one out of the four available contexts currently identified by context identification instance 78*b*. One way in which message priority indications can be provided in this example can be by a user marking analytical device data from P1A and P1B as "unimportant" using a GUI 24A of a POC-DMS 12A, although the other message priority indication approaches discussed in this document may also be used.

Therefore, the time-series of analytical device data received from P1A can be schematically illustrated in time-series 90*a*. Between T=00:00 and T=05:00, P1A is in context "1", indicated at region 91 of the time-series 90*a*. Between T=05:00 and T=12:00, P1A is in context "2", indicated at region 92 of the time-series 90*a*.

The time-series of analytical device data received from P2A can be schematically illustrated in time-series 90*b*. Between T=00:00 and T=06:00, P1A is in context "2", indicated at region 93 of the time-series 90*b*. Between T=06:00 and T=12:00, P1A is in context "1",indicated at region 94 of the time-series 90*b*.

The plurality of message priority indications in respect of analytical device data in context "1" received from either P1A or P2A can be used to generate message filter configuration F1(x) 72*a*.

The plurality of message priority indications in respect of analytical device data in context "2" received from either P1A or P2A can be used to generate message filter configuration F2(x) 72*b*.

Message filter configurations F1(x) and F2(x) may then be stored in memory 96.

In this way, a plurality of message filter configurations 23*a*, 23*b* may be generated dependent on the context in which an analytical device is used. Optionally, a message filter configuration may be assembled from message priority indications originating from analytical device data output from different analytical devices at different times, but in a shared context, but this is not essential.

The use of a state machine to track the context of an analytical device P1A may be beneficial because it can enable order dependence between contexts to be enforced based on the arrangement of the transitions of the state machine. For example, the transition of an analytical device P1A between an accident and emergency department context and a teaching context may be understandable in a teaching hospital where it can be physically possible for an analytical device to be exchanged between such departments. However, it may not be possible for an analytical device P2A to be taken from a teaching context into a home visit context.

A skilled person can appreciate that the use of a finite state machine to track the context of an analytical device may not be essential, and can be used in this description to illustrate the concept of context tracking. Finite state machines may be beneficially used to track a finite set of contexts with designed context transition rules. Alternatively, or in combination, the context identification may employ one, or a combination, of hierarchical state machines. Alternatively, the determination the presence of an analytical device in a specific context can be made based on a voting scheme detected by stimuli received from the analytical device or POC-DMS, or a Bayesian classifier.

In an example, a unique instance of the context identification engine can be maintained for each active (switched on) analytical device in the first network 10A. This can enable a plurality of portable analytical devices P1A-P7A to be tracked simultaneously in different contexts, or as they move between different contexts and for the message handling from each portable analytical device of the plurality of portable analytical devices P1A-P7A to be filtered based on the context of each portable analytical device of the plurality of analytical devices P1A-P7A.

Optionally, if a unique instance 78*a* of the context identification engine 78 of an active (switched on) analytical device cannot associate the analytical device with a context using the context identification engine 78 based on a contemporary set of inputs, the context can be determined to be an indeterminate (unknown) state which can provide a default message filter configuration for message priority choices relating to analytical device status data from the POC in the indeterminate context.

In an example, the context of a single portable analytical device may be modelled by an instance in the context identification engine as one or more states in a finite state machine 78 (abbreviated to state machine). Inputs 76 to the finite state machine 78 may be obtained from any of the data available to the POC-DMS 10A in the first network, which can provide a rich source of input data for the context determination made by the context determination engine.

For example, the finite state machine 78 may take, as inputs 76 from the POC-DMS 10A in the first network, one or more of network configuration information of a single analytical device or a plurality of analytical devices, analytical device internal operation information, user logon information to a specific POC, user certification data, geographical location data of an analytical device, and information concerning the assay type performed on a specific analytical device. Many more sources of information may be obtained from at least the POC-DMS 10A to enable a determination of context.

For example, the state machine 78 may provide, as outputs, a plurality of message filter configurations 72*a*, 72*b*, 72*c*, and 72*d*. Each message filter configuration of the plurality of message filter configurations 72*a*, 72*b*, 72*c*, and 72*d* can correspond to a state in the state machine 78.

When an individual analytical device P1A is identified, a unique instance of the state machine 78 can be instantiated within the context identification engine. The unique instance of the state machine 78 can track the context relevant to individual analytical device P1A. If the context relevant to individual analytical device PIA cannot be identified, the unique instance of the state machine 78 modelling the context of individual analytical device P1A can remain in the indeterminate state 82.

For one more states of the unique instance of the state machine 78 that models the context of an individual analytical device P1A, there can be an instance of the message filter configuration. In a case where only one instance of state machine 78 is present, modelling the context of individual analytical device P1A between three contexts and one undetermined context, four instances of the message filter configuration 72*a*, 72*b*, 72*c*, and 72*d* can be provided.

According to an embodiment, the one, or more contexts can be determined in various ways. In particular, a context determination may be based on one, or any combination of, data enumerated in the following (i) The context determination may be based on network configuration data at least partially characterizing the device configuration of the first analyzer network. For example, the presence or absence of certain types of analytical device on a network 10A can enable the identification of a device context. For example, certain types of analytical devices may not be portable and can only be used in pathology laboratories, whereas other types of analytical devices can be portable. Furthermore, a network server may maintain a registry of network addresses. When analytical device data is received from within an expected range of network addresses, a determination may be made using the registry of network addresses that the analyzer data has been received from one of several device contexts.

(ii) The context determination may be based on internal configuration data of the at least one analytical device that sent the message subsequently assigned the message priority indication. For example, the type of message sent by the analytical device may itself enable identification, or inference, of an operating context of the analytical device. Internal configuration data may relate to the tests, which an analytical device can be capable of performing, information about the software configuration of the analytical device and firmware version, information about the maintenance condition of the analytical device, and the like.

(iii) The context determination may be based on battery life data of the at least one analytical device that sent the message subsequently assigned the message priority indication. For example, an analytical device used in the context of a home visit nurse may not be recharged as frequently as an analytical device used in the context of an accident and emergency room (owing to the proximity of more charging sockets) and therefore the battery life data and/or recharging data relating to an analytical device may enable some inference about the context of use of an analytical device.

(iv) The context determination may be based on quality control data of the at least one analytical device that sent the message subsequently assigned the message priority indication. Quality control data related to results provided by an analytical device can provide an insight into the maintenance condition of an analytical device. For example, a frequently used analytical device might require recalibration more frequently.

(v) The context determination may be based on an assay type performed on the at least one analytical device associated at, or close to, the time that the message priority indication was generated. For example, specific assay types may only be offered in certain departments of a hospital, and thus the receipt of message priority indications relating to analytical device data of a specific assay type enables further inference of the context of origin of the analytical device data.

(vi) The context determination may be based on the time at which the message priority indication and/or the analytical device data was generated. For example, the time of generation of an item of analytical device data may be compared to a staff shift pattern to provide further information to infer a use context (with use by a certain subset of staff enabling inference of a use context).

(vii) The context determination may be based on location data of the at least one analytical device and/or first analytical device management system. For example, the location data may comprise a GPS coordinate of one or more analytical devices. The location data may comprise a separation distance between the analytical device and its analytical device management system (POC-DMS) 12A. The location data may comprise a geo-fencing condition, wherein one or a plurality of geographical demarcations are defined, and the presence, or not, of the plurality of analytical devices inside the geo-fenced regions are represented by a binary vector, for example.

(viii) The context determination may be based on operator data and/or certification data of the at least one analytical device and/or first analytical device management system.

(ix) The context determination may be based on the content of the analyzer data. For example, as a user logs on to the analytical device P1A, the analytical device management system (POC-DMS) 12A may interrogate a user database to obtain user classification data about the user. For example, the user classification data may comprise a user job title, user certification status, shift plan data of the user, and the like.

(x) The context determination may be based on a count of the number of messages received from the at least one analytical device.

(xi) The context determination may be based on log data defining a previous configuration of the first analyzer network and/or the first analytical device management system POC DMS1, and metadata obtained from a further information source.

A skilled person can appreciate that many other sources of data may be used by a context identification engine to enable the identification of a use context of an analytical device.

Once the data processing agent 23 has generated one or more message filter configuration 72, whether via a rule-based approach as illustrated in FIG. 6 or with additional contact information as illustrated in FIG. 7 and FIG. 8, the one or more message filter configuration 72 may optionally be applied to subsequent analytical device data originating from within network 10A.

In other words, the one or more message filter configuration 72 may provide a degree of feedback to the same message that enabled the POC-DMS 12A to generate message filter configurations 72.

The data processing agent 23 may, upon completion of the message filter configuration 72, store the message filter configuration 72 in a data storage unit collocated with the data processing agent 23, or at a remote location.

Furthermore, the one or more message filter configuration 72 may be transmitted to one or more further networks 12B and/or one or more further analytical device management systems POC-DMS 12B. When the one or more message filter configuration 72 have been received by the one or more further networks 12B and/or one or more further analytical device management systems POC-DMS 12B, the message filter configuration 72 generated in the first network 10A may be applied to the filtering for display of analytical device data generated from within the one or more further networks 10B.

In this way, the data processing agent 23 can assemble, or update, one or more "smart filters" using message priority indications generated in the first network 10A. The one or more "smart filters" may then be electronically communicated to further networks 10B comprising analytical devices, so that improved message filtering performance obtained at the first network 10A can also be experienced in the further networks 10B.

Optionally, the analytical device management system in the further network or networks 10B POC-DMS 12B can be configured to request, from the data processing agent 23, a version of the message filter configuration 72 generated by the data processing agent 23. Upon receiving a request from the analytical device management system in the further network or networks 10B POC-DMS 12B for the updated version of the message filter configuration 72 generated by the data processing agent 23, the data processing agent 23 can be configured to transmit, to the analytical device management system in the further network or networks 10B POC-DMS 12B, the message filter configuration 72.

According to an embodiment, the message filter configuration can comprise, for at least one type of message, a plurality of priority elements corresponding to different identified contexts of the first analyzer network 10A and/or the first analytical device management system 12A, and/or the at least one at least one analytical device P1A from which the message priority indication originated.

According to an embodiment, it can be further provided to receive, at the data processing agent 23, a request to send the at least one message filter configuration to a second analytical device management system 12B in a second analyzer network 10B, and/or to a second analytical device of medical samples P1B in the second analyzer network; to receive, at the data processing agent 23 information defining the geographical location and/or context of the second analytical device management system 12B and/or the second analytical device P1B; to obtain at least one message filter configuration based on the information defining the geographical location and/or context of the second analytical device management system 12B and/or the second analytical device P1B; and to send the obtained at least one message filter configuration to the second analytical device management system 12B and/or the second analytical device P1B.

According to this embodiment, the message filter configuration 72 can be adjusted based upon the location at which the second analytical device management system 12B and/or the second analytical device P1B is located. National health systems can often be organized along different lines. Automatically generated message filter configurations 72 applicable on the first country may be less applicable in a second country, for example.

According to an embodiment, it can be further provided to compare the message filter configuration to a reference message filter configuration; to identify a deviation between the message filter configuration and the reference message filter configuration; and to update the message filter configuration to reduce or to remove the deviation between the message filter configuration and the reference message filter configuration.

There can be a small possibility that through operator error, messages that may have an overriding importance can be assigned, at an analytical device management system POC-DMS 12A, a lower priority than they should be given. For example, a repeated warning message displayed at an analytical device management system POC-DMS 12A drawing attention to an expired calibration deadline could be hypothetically repeatedly assigned the category "unimportant" by an uninformed user of the analytical device management system POC-DMS 12A. It can clearly be undesirable for such an unwanted input to result in the generation of a message filter configuration, which can be used in the originating network 10A, or forwarded to a further network 10B.

According to the present embodiment, a generated message filter configuration can be compared to a reference message filter configuration. For example, the reference message filter configuration can contain overriding message filter records for system messages that have an overriding importance, such as calibration warnings or patient safety warnings. A deviation between the reference message configuration can be reset or removed before the message filter configuration can be applied at an analytical device management system POC-DMS 12A in the first network 10A or forwarded to the further networks 10B to be installed on an analytical device management system POC-DMS 12B in the further network. Accordingly, the propagation of incorrect or partially correct message filter configurations can be avoided.

According to another embodiment, an apparatus 40 configured to host a data processing agent 23 for processing data from an analytical device 20 can be provided. The apparatus can comprise a communications interface 54, a data memory 44, and a processor 47 coupled to the communications interface 54 and the data memory 44.

The communications interface 54 can be configured to receive one or more items of data comprising a priority indication transmitted from the first analytical device management system 12A to the data processing agent 23 via a communications network 10A.

The processor 47 can be configured to receive, from the communications interface 54, the message priority indication indicating a priority assigned to an item of analytical device status data, and to generate or update, a message filter configuration stored in the data memory 44 based on the message priority.

The communications interface 54 can be further configured to communicate the message filter configuration, or a portion thereof, to a second analyzer network 10B comprising a second analytical device P1B of medical samples.

The apparatus 40 that hosts the data processing agent 23 may be a stand-alone server connected to the first network 10A. The apparatus 40 that hosts the data processing agent 23 may be the computer hosting the analytical device management system POC-DMS 12A. In such a case, the message priority indications from the analytical device management system POC-DMS 12A may need to be transmitted from the analytical device management system POC-DMS 12A to the stand-alone server connected to the first network 10A.

The apparatus 40 that hosts the data processing agent 23 may be a cloud server accessible via the Internet (as provided by the Amazon EC2™ or the Microsoft Azure™ services, as two examples). In such a case, the message priority indications from the analytical device management system POC-DMS 12A may need to be transmitted over the Internet to such a cloud service.

The message filter configuration 72 may be updated continuously by the data processing agent 23 (in other words, in "real-time") as message priority indications are entered into, or detected, by the analytical device management system POC-DMS 12A, with a continuously recalculated message filter configuration 72 being communicated from the data processing agent 23 to further networks 10B.

Alternatively, the message filter configuration 72 may be updated by the data processing agent 23 in a batch mode. The analytical device management system POC-DMS 12A may store, either in local, network, or cloud storage, an archive of message priority indications. The data processing agent 23 can then poll the local, network, or cloud storage to receive the stored archive of message priority indications. Optionally, the data processing agent 23 can place a time restriction or other form of restriction on the amount of message priority indications received to reduce the amount of data transferred to the data processing agent 23. In other words, it can be possible, but not essential for the data processing agent 23 to generate the message filter configuration in "real-time". Optionally, the data processing agent 23 may generate the message filter configuration according to a constant schedule, such as once a day at 3 AM.

According to an embodiment, it can be further provided to display, via a user interface 24A of the first analytical device management system 12A or the first analytical device P1A in the first analyzer network 10A, the analytical device status data generated by the first analytical device; to receive, via the user interface 24A of the first analytical device management system 12A or the first analytical device P1A, the message priority indication; and to transmit the message priority indication to the data processing agent 23.

A display of the POC-DMS 12A, 12B or an associated mobile device such as smartphone or tablet 26A, 26B may be optimized for user responsiveness. When a network of analyzers is generating hundreds, or thousands of messages a minute, significant communication overhead can build up between the data processing agent 40 (server) and the POC-DMS 12A, 12B, or associated mobile device such as smartphone or tablet 26A, 26B. The ability of the data processing agent 40 to filter messages based on the salience of a particular message to a user as observed by the data processing may enable to communication, and/or display overhead to be significantly reduced.

For example, the data processing agent 40 and an application providing a GUI 100 executing on the POC-DMS 12A, 12B or an associated mobile device such as smartphone or tablet 26A, 26B GUI 100 can establish a synchronized data binding between analytical device status messages received at the data processing agent 40, and messages displayed on the GUI 100.

Optionally, a synchronized data binding between the data processing agent 40 and the POC-DMS 12A, 12B and/or an application providing a GUI 100 executing on an associated mobile device such as smartphone or tablet 26A, 26B can be established based on the message filter configuration 72. For example, a synchronized data binding may not be established for analytical device status messages of a type previously marked "unimportant" by a user.

In a data binding process, each data change can be reflected automatically by the elements that are bound to the data. By reducing the number of "unimportant" messages that are displayed at the GUI 100, processing load on the data processing agent 40, or another server hosting the data processing agent 40, can be reduced.

Typical examples of protocols enabling data binding can be "Backbone.js"™, "Polymer"™, "Vue.js"™, "AngularJS"™, "Google Web Toolkit"™, "Windows Presentation Foundation"™, and the like.

Figure 9A:
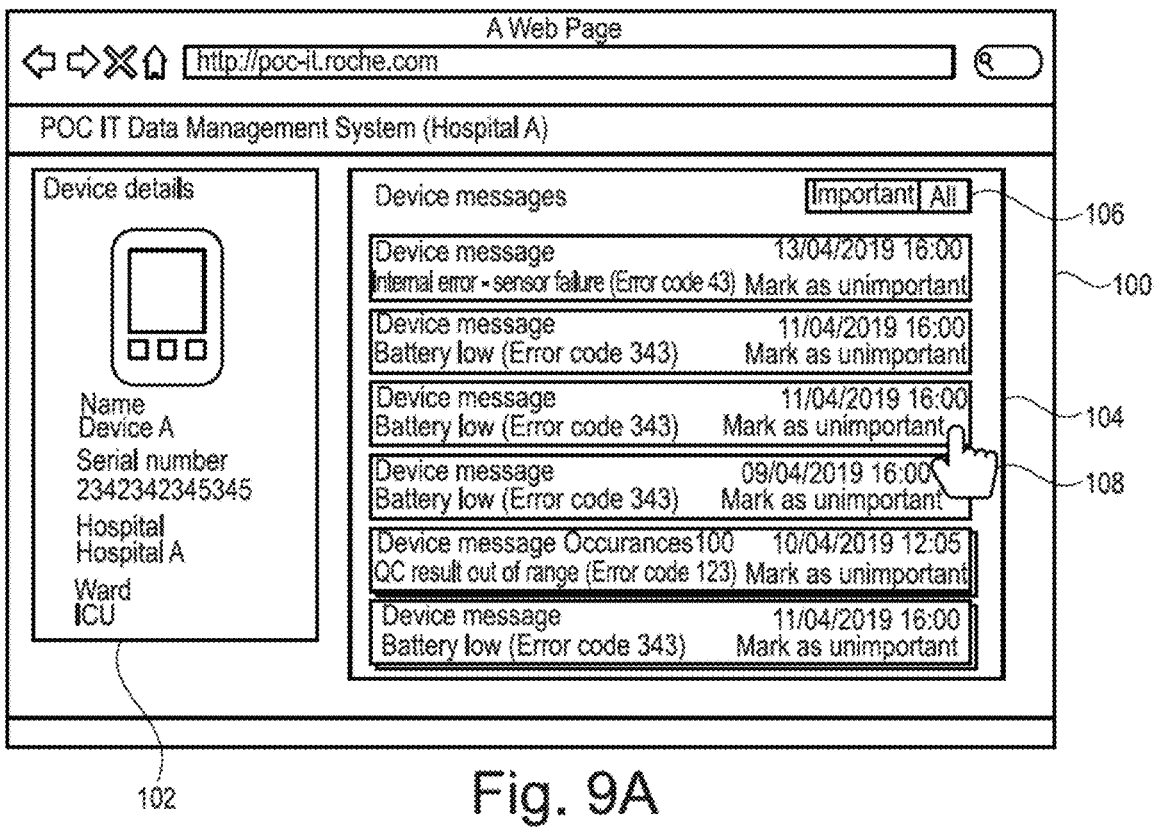
FIG. 9A illustrates schematically a user adding a message priority indication related to an analytical device message via a GUI on an analytical device management system (POC-DMS) according to an embodiment of the present disclosure.

FIG. 9A schematically illustrates a user adding a message priority indication related to an analytical device message via a GUI 100 on an analytical device management system (POC-DMS).

Analytical device messages can be regularly sent to the POC DMS 12A. Those messages may be marked by the user as "unimportant" using a dialog button or other input means 108 of the GUI (this is one example of a message priority indication). In this way, analytical device messages in a feed of events that were received at the POC DMS 12A can be filtered by the message filter configuration generated based on the user marking as "unimportant", so that the messages can be automatically hidden from the user. Another effect of this can be that the message feed remains clear and only informs the user about the most important messages. Furthermore, messages having a high relevance may be cached in short-term memory such as RAM, whereas less relevant messages may be stored in long-term memory, such as a hard disk drive or solid-state memory, or on a remote server.

The GUI 100 of the analytical device management system (POC-DMS) may display a thumbnail 102 indicating a current selected analytical device (device). The messages from the current selected analytical device can be displayed in the device message feed 104. As a safety feature, the device message feed may enable selection of the display of messages (analytical device messages) across various modes, where one mode always enables the display of "all" messages. In the illustrated case, the selector 106 can show that only messages previously given a priority as "important" are displayed. A cursor 108 operated by user can be used to "Mark as an unimportant" the analytical device message "battery low (error code 343).

Figure 9B:
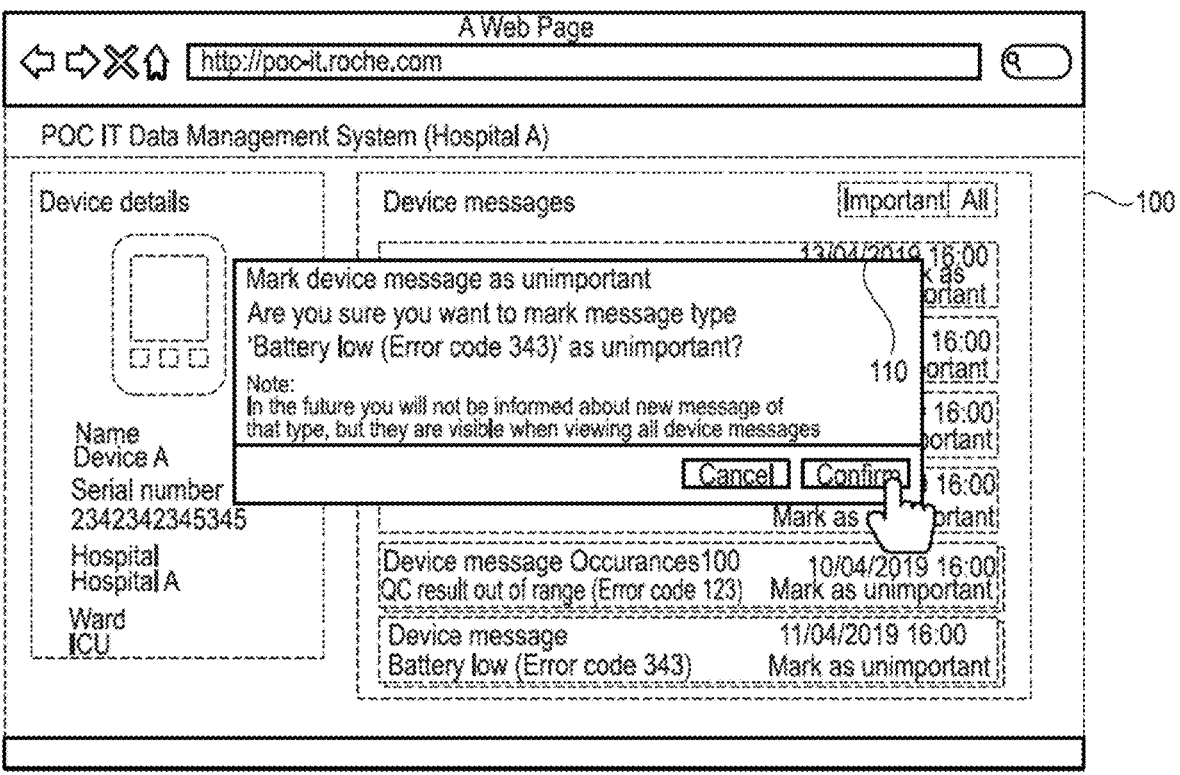
FIG. 9B illustrates schematically a user adding a message priority indication related to an analytical device message via a GUI on an analytical device management system (POC-DMS) according to an embodiment of the present disclosure.

FIG. 9B schematically illustrates a user adding a message priority indication related to an analytical device message via a GUI on an analytical device management system (POC-DMS).

Optionally, after the user has operated the cursor 1082 mark the analytical device message "battery low (error code 343)" as unimportant, a dialog box 110 can be displayed enabling a user to confirm or cancel the message priority indication selection made.

FIG. 9C schematically illustrates further GUI features of an analytical device management system (POC-DMS).

In particular, when the view "all" button of the GUI 100 is selected, messages which have previously been marked as unimportant can be displayed in the message feed 104, optionally with a different color, for example. This can enable a safety check of filtered messages to be performed by a user to make sure that important messages are not being omitted from the feed.

According to an embodiment, it can be further provided to receive, at the data processing agent 23, a plurality of message filter configurations 72 generated from a respective plurality of analyzer networks and to process, at the data processing agent 23, the plurality of message filter configurations 72 to obtain a combined message filter configuration.

According to an embodiment, it can be further provided to receive a request from an analytical device management system (POC-DMS) in a further network comprising analytical devices and to communicate the combined message filter configuration to the analytical device management system (POC-DMS) in the further network, and/or communicating the combined message filter configuration to one or more analytical devices in the further network.

According to an embodiment, it can be further provided to receive, at the second analytical device management system 12B in the second analyzer network 10B, at least a portion of the message filter configuration generated by the data processing agent 23; to receive, at the second analytical device management system 12B, a further item of analytical device status data generated by a second analytical device P1B in the second analyzer network 10A; to compare the further item of analytical device status data to the at least a portion of the message filter configuration; and to display the further item of analytical device status data to an operator of the second analytical device management system 12B according to a modality indicated by the message filter configuration as being applicable for the display of the further message.

According to an embodiment, the method can further comprise receiving, at the second analytical device management system 12B in the second analyzer network 10B, at least a portion of the message filter configuration 72 generated by the data processing agent 23; receiving, at the second analytical device management system 12B, a further item of analytical device status data generated by a second analytical device P1B in the second analyzer network 10B; comparing the further item of analytical device status data to at least a portion of the message filter configuration 72; and displaying the further item of analytical device status data to an operator of the second analytical device management system 12B according to a display modality indicated by the message filter configuration as being applicable for the display of the further message.

FIG. 10A schematically illustrates the installation of a message filter configuration generated by the data processing agent 23 on an analytical device management system (POC-DMS) in a further network 10B.

Optionally, the analytical device management system (POC-DMS) 12B in a second network 10B may automatically poll the data processing agent 23 for an updated or new message filter configuration, and request permission to install the updated or new message filter configuration using a pop-up box 122.

Optionally, a user may request, via the GUI 100, an updated or new message filter configuration, and confirm permission to install the updated or new message filter configuration using a pop-up box 122.

The GUI 120 can optionally be displayed, for example, on a display of an analytical device management system (POC-DMS) 12B in a second network 10B remote from the first network 10A used to generate the message filter configuration.

Figure 10B:
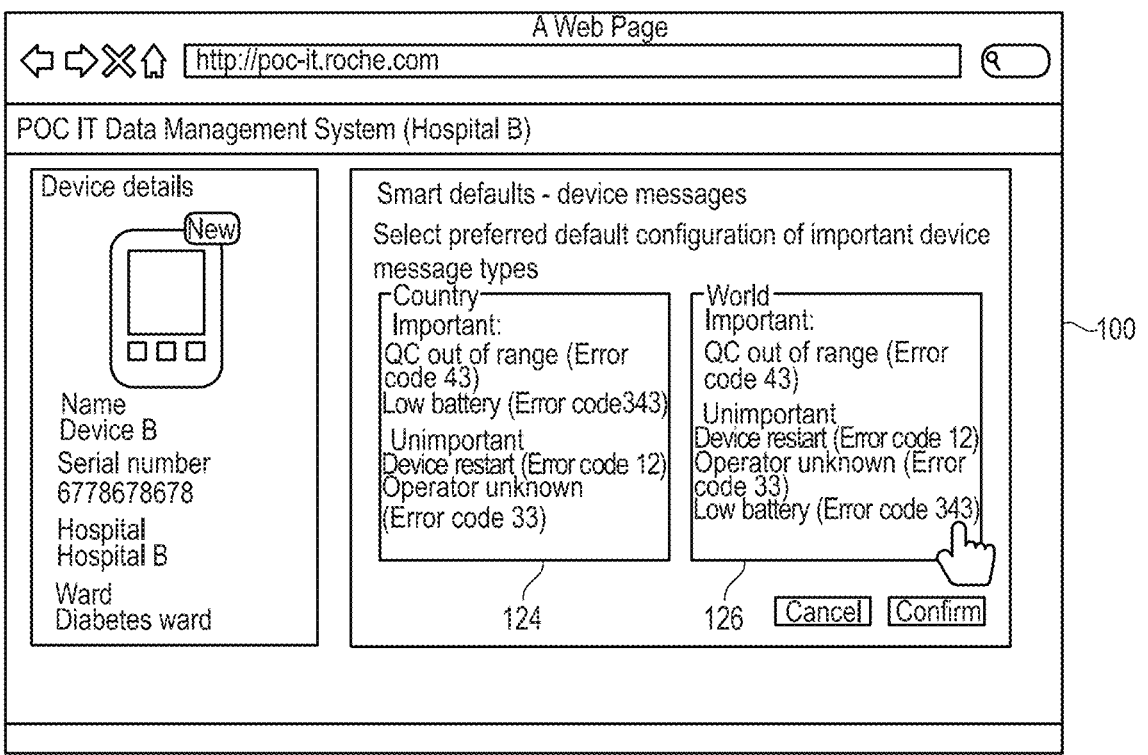
FIG. 10B illustrates schematically the installation of a message filter configuration on an analytical device management system (POC-DMS) according to an embodiment of the present disclosure.
Figure 11:
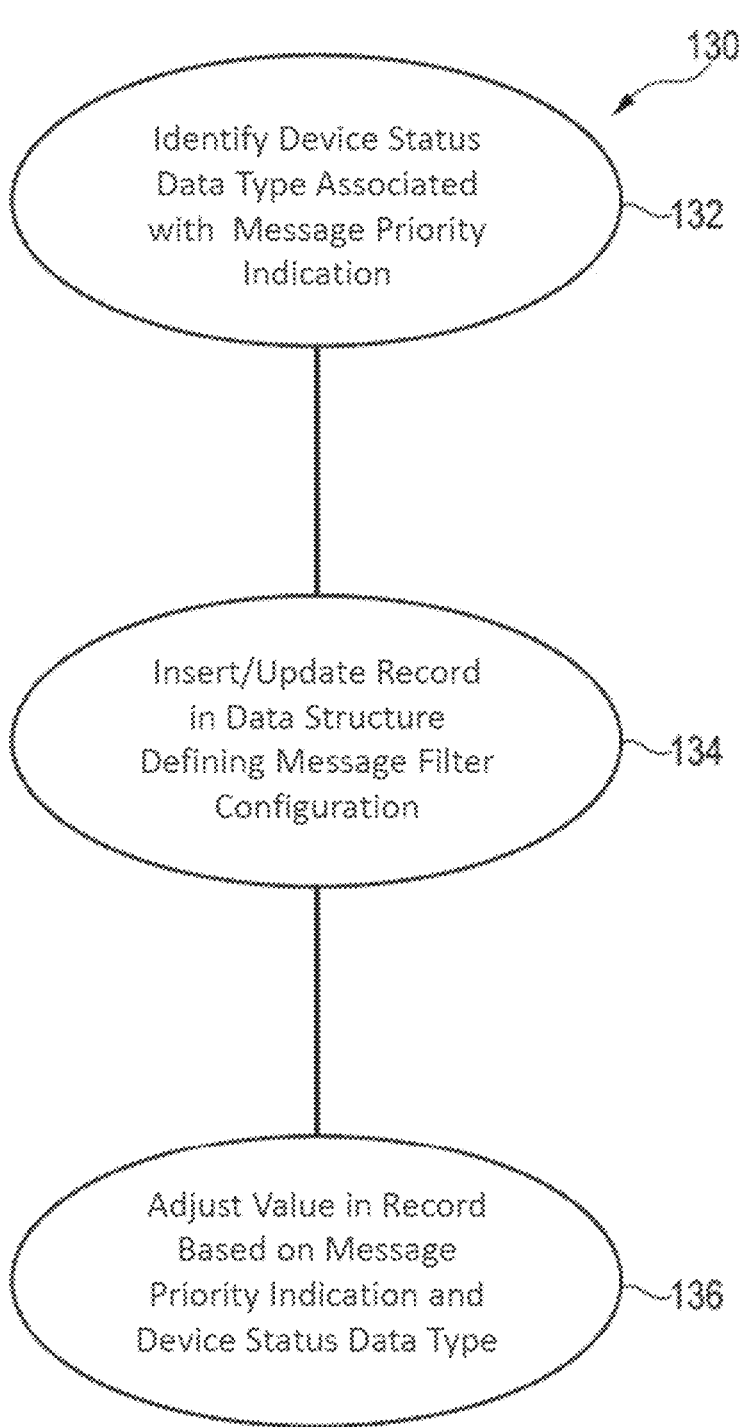
FIG. 11 illustrates schematically illustrates a flow diagram according to the method of FIG. 1 according to an embodiment of the present disclosure.

FIG. 10B schematically illustrates the installation of a message filter configuration on an analytical device management system (POC-DMS) in the second network 10B using a GUI 100 on an analytical device management system (POC-DMS) 12B in a second network. In this case, the user may choose between a message filter configuration obtained from a specific country 124, or a global message filter configuration 126.

Optionally, the analytical device management system 12B in the second analyzer network 10B can be configured to directly archive analytical device status data from at least one analytical device P1B-P7B based on the message filter configuration. For example, the analytical device management system 12B can be configured to store an item of received analyzer status data in non-volatile memory, or in a database, and not display the analytical device status data on a graphical user interface 24B of the analytical device management system 12B based on the message filter configuration.

As such, in a specific example, it can be seen that when an analytical device message type is marked as "unimportant" by the user, the analyzer management system (POC-DMS) in the first network 10B can generate a message to inform the data processing agent 23 about the change of that preference, together with the country information. Based on collected preferences from all correct hospitals, the most common preference for each type of analytical device message can be calculated for both the country, and the world.

When a new analytical device "B" arrives in hospital "B", the user can be presented with a choice download smart default settings for that type of device. The user may choose to take the smart defaults for their country or for the world. In this example, the user can be presented with the possible default configuration based on the country's most preferred configuration of device messages where only the device message "QC out of range" and "low battery" can be the only important message types or the world's most preferred configuration of device messages in which "low battery" message can typically be flagged as unimportant. Based on the selection made by the user, the upcoming device message can automatically be flagged with the selected set of important versus unimportant settings.

According to another embodiment, a networked system for analytical device management 10 can be provided. The network system can comprise a first set of one or more analytical devices P1A-P7A configured to analyze patient medical samples and to generate analytical device status data; a first analytical device management system 12A configured to receive analytical device status data from one or more analytical devices comprised in the first set of one or more analytical devices P1A-P7A; an apparatus 40 configured to host a data processing agent 23 for processing data received from the first analytical device management system 12A and/or the first set of one or more analytical devices P1A-P7A; a second set of one or more analytical devices P1B-P7B configured to analyze patient medical samples; a second analytical device management system 12B configured to receive analytical device status data from one or more analytical devices comprised in the second set of one or more analytical devices P1B-P7B; and a communication network 21 configured to communicatively connect the first analytical device management system 12A, the apparatus configured to host the data processing agent 23, and second analytical device management system 12B.

The apparatus 40 can be configured to receive a message priority indication generated by the first analytical device management system 12A and/or the at least one analytical device P1A-P7A in the first analyzer network 10A, indicating a priority assigned to the message.

The apparatus 40 can be configured to generate or to update a message filter configuration based on the message priority of the first device message.

The apparatus 40 can be configured to communicate the message filter configuration, or a portion thereof, to the second analytical device management system 12B and/or the second set of one or more analytical devices P1B-P7B.

The second analytical device management system 12B and/or at least one analytical device in the second set of one or more analytical devices P1B-P7B can be configured to receive a further item of analytical device status data from within the second analyzer network, and to display the further item of analytical device status data according to the priority assigned in the received message filter configuration.

According to another embodiment, a computer program element comprising computer-readable instructions for controlling the above apparatus, which, when being executed by a processing unit of the apparatus, can be configured to perform the above method steps.

According to another embodiment, a computer readable medium or signal having stored, or encoded thereon, the above computer program element can be provided.

According to another embodiment, a method of operating an analytical device management system 12B and/or an analytical device P1B-P7B can be configured to receive a plurality of items of analytical device status data from at least one analytical device P1B-P7B in a second analyzer network 10B; to request, via a communications network, from an apparatus 40, a message filter configuration configured to filter at least one of the plurality of items of analytical device status data received from the second analyzer network 10B, to receive, via the communications network 10B, the message filter configuration from the apparatus 40; and to filter at least one item of analytical device status data in the plurality of items of analytical device status data according to the message filter configuration to generate a filtered plurality of messages.

According to an embodiment, the method can further comprises displaying, via a user interface 24B of the analytical device management system 12B, the filtered plurality of items of analytical device status data.

According to an embodiment, the analytical device management system can store analytical device status data of a type that has been assigned a first status in long-term memory, optionally a hard disk drive or solid-state memory. The analytical device management system can store analytical device status data of a type that has been assigned a second status, in short-term memory, optionally Random Access Memory (RAM). For example, analytical device status data of a type that has been assigned a low status, or the status "unimportant," can be stored in the long-term memory. Analytical device status data of a type that has been assigned a high status, or "important", can be stored in the short-term memory.

According to an embodiment, displaying, via a user interface 24B of the analytical device management system 12B, the filtered plurality of items of analytical device status data can comprise reading the analytical device status data of a type that has been assigned a second status from the short term memory, and displaying the analytical device status data that has been read from the short term memory.

According to another embodiment, an apparatus configured to host an analytical device management system for processing data from one or more analytical devices of medical samples can be provided. The apparatus can comprise a communications interface, a data memory, a display interface, and a processor coupled to the communications interface and the data memory.

The communications interface can be configured to receive a plurality of items of analytical device status data from at least one analytical device in a second analyzer network, and to request, via a communications network, from an apparatus according to the second aspect, a message filter configuration configured to filter at least one of the plurality of messages received from the second analyzer network. The communications interface can be configured to receive, via the communications network, the message filter configuration from the apparatus according to the second aspect and to store it in the data memory. The processor can be configured to filter at least one item of analytical device status data in the plurality of items of analytical device status data according to the message filter configuration stored in the data memory to generate a filtered plurality of analytical device status data.

According to an embodiment, the display interface can be configured to generate a graphical user interface capable of displaying the filtered plurality of analytical device status data.

According to an embodiment, the data memory can comprise long-term memory and short-term memory. For example, the long-term memory may comprise non-volatile memory such as a hard disk drive or a solid-state drive. For example, the short-term memory may comprise random access memory (RAM). Analytical device status data of a type that has been assigned a first status can be stored in the long-term memory. Analytical device status data of a type that has been assigned a second status can be stored in the short-term memory. For example, analytical device status data of a type that has been assigned a low status, or the status "unimportant," can be stored in the long-term memory. Analytical device status data of a type that has been assigned a high status, or "important," can be stored in the short-term memory.

According to an embodiment, the apparatus can be configured to display, via the display interface, the filtered plurality of items of analytical device status data by reading the analytical device status data of a type that has been assigned a second status from the short term memory, and displaying, via the display interface, the analytical device status data that has been read from the short term memory.

According to another embodiment, an apparatus configured to host an analytical device management system for processing data from one or more analytical devices can be provided. The apparatus can comprise a communicator, data storage, and a processor coupled to the communicator and the data storage.

The communicator can be configured to receive a plurality of items of analytical device status data from at least one analytical device in a second analyzer network, and to request, via a communications network, from an apparatus according to the second aspect, a message filter configuration configured to filter at least one of the plurality of messages received from the second analyzer network. The communicator can be configured to receive, via the communications network, the message filter configuration from the above apparatus and to store it in the data storage. The processor can be configured to filter at least one item of analytical device status data in the plurality of items of analytical device status data according to the message filter configuration stored in the data memory to generate a filtered plurality of messages.

It is noted that terms like "preferably," "commonly," and "typically" are not utilized herein to limit the scope of the claimed embodiments or to imply that certain features are critical, essential, or even important to the structure or function of the claimed embodiments. Rather, these terms are merely intended to highlight alternative or additional features that may or may not be utilized in a particular embodiment of the present disclosure.

Having described the present disclosure in detail and by reference to specific embodiments thereof, it will be apparent that modifications and variations are possible without departing from the scope of the disclosure defined in the appended claims. More specifically, although some aspects of the present disclosure are identified herein as preferred or particularly advantageous, it is contemplated that the present disclosure is not necessarily limited to these preferred aspects of the disclosure.

The invention claimed is:

1. A computer implemented method for generating a message filter configuration based on a message priority indication received from a first analyzer network, wherein the first analyzer network comprises an analytical device configured to generate analytical device status data, the method comprising:

receiving, at a data processing agent, an analytical device status data message generated by the analytical device in the first analyzer network;

determining, based at least in part on network configuration information associated with the first analyzer network, a use context associated with the analytical device;

identifying a type of the analytical device status data message, wherein the analytical device status data message comprises condition data associated with the analytical device including one or more of a hardware heartbeat, a specific hardware fault, overheating information, lid jam information, reagent information, device temperature information, or count of assays performed;

determining, at the data processing agent, a message priority indication assigned to the analytical device status data message;

determining, at the data processing agent, a record for a message filter configuration associated with the identified type of the analytical device status data message and the use context, based at least in part on the message priority indication;

updating, by the data processing agent, a data structure defining the message filter configuration, based at least in part on the record associated with the identified type of the analytical device status data and the use context; and communicating the data structure defining the message filter configuration, or a portion thereof, to a second analyzer network comprising a second analytical device.

2. The computer implemented method according to claim 1, further comprising, receiving, at the data processing agent, a plurality of message priority indications from one or more further analyzer networks, and wherein the message filter configuration is generated based on the plurality of message priority indications.

3. The computer implemented method according to claim 1, wherein the identified type of data of analytical device status data comprises feedback information associated with the analytical device.

4. The computer implemented method according to claim 3, wherein the feedback information comprises one or more of a software or firmware update request, user login information, audit log message, and memory capacity information.

5. The computer implemented method according to claim 1, wherein the use context associated with the analytical device is determined based on one or more of:

network configuration data at least partially characterizing a device configuration of the first analyzer network, internal configuration data, or internal sensor data, of the analytical device that sent the message subsequently assigned the message priority indication, battery life data of the analytical device that sent the message subsequently assigned the message priority indication, quality control data generated by the analytical device that sent the message subsequently assigned the message priority indication, an assay type performed on the analytical device of medical samples at a time proximate to when the message priority indication was generated, the time at which the message priority indication and/or the message was generated, location data of the analytical device and/or a first analytical device management system, operator data and/or certification data of the analytical device and/or the first analytical device management system, a content of the analytical device status data, a number of items of analytical device status data received from the analytical device, log data defining a previous configuration of the first analyzer network and/or the first analytical device management system, and metadata obtained from a further information source such as a user logon server or a certification server.

6. The computer implemented method according to claim 1, wherein the message filter configuration comprises, for at least one type of message, a plurality of records corresponding to message priorities assigned to different identified use contexts of the first analyzer network and/or a first analytical device management system and/or the analytical device from which the message priority indication originated.

7. The computer implemented method according to claim 1, further comprising, receiving, at the data processing agent, a request to send the message filter configuration to a second analytical device management system in a second analyzer network and/or to a second analytical device of medical samples in the second analyzer network;

receiving, at the data processing agent, information defining at least one of a geographical location or a use context of the second analytical device management system and/or the second analytical device;

obtaining at least one message filter configuration based on the information defining at least one of the geographical location or the use context of the second analytical device management system and/or the second analytical device; and sending the obtained at least one message filter configuration to the second analytical device management system and/or the second analytical device.

8. The computer implemented method according to claim 1, further comprising, comparing the message filter configuration to a reference message filter configuration;

identifying a deviation between the message filter configuration and the reference message filter configuration; and updating the message filter configuration to reduce or to remove the deviation between the message filter configuration and the reference message filter configuration.

9. The computer implemented method according to claim 1, further comprising, displaying, via a user interface of a first analytical device management system or the analytical device in the first analyzer network, the analytical device status data generated by the analytical device;

receiving, via the user interface of the first analytical device management system or the analytical device, the message priority indication; and transmitting the message priority indication to the data processing agent.

10. The computer implemented method according to claim 1, wherein determining the record for the message filter configuration comprises:

determining, based at least in part on the message priority indication, a binary indication of whether a received message having the identified type of analytical device status data should be displayed.

11. The computer implemented method according to claim 1, wherein determining the record for the message filter configuration comprises:

calculating a category importance ratio associated with the identified type of analytical device status data, based at least in part on a first number of messages received by the data processing agent, and a second number of the messages received having the assigned priority indication.

12. The computer implemented method according to claim 1, wherein determining the use context associated with the analytical device comprises:

determining a network address associated with the analytical device status data message; and determining whether the network address is within a range of network addresses associated with a network server.

13. The computer implemented method according to claim 1, wherein determining the use context associated with the analytical device comprises at least one of:

determining that the analytical device is being used in a teaching context;

determining that the analytical device is operating in an accident ward;

determining that the analytical device is operating in a laboratory; or determining that the analytical device is operating in a home visit context.

14. The computer implemented method according to claim 1, further comprising tracking the use context associated with the analytical device using a finite state machine, wherein tracking the use context comprises:

determining, using the finite state machine, a previous use context associated with the analytical device; and validating, using the finite state machine, a transition between the previous use context and the use context.

15. An apparatus configured to host a data processing agent for processing data from an analytical device, the apparatus comprising:

a communications interface, wherein the communications interface is configured to receive one or more items of data comprising a message priority indication transmitted from a first analytical device management system to the data processing agent via a communications network;

a data memory; and a processor coupled to the communications interface and the data memory, wherein the processor is configured to:

receive, from the communications interface, a message priority indication indicating a priority assigned to an item of analytical device status data, determine, based at least in part on network configuration information associated with the communications network, a use context associated with the analytical device;

identify a type of the analytical device status data associated with the message priority indication, wherein the analytical device status data comprises condition data associated with the analytical device including one or more of a hardware heartbeat, a specific hardware fault, overheating information, lid jam information, reagent information, device temperature information, or count of assays performed, determine a record for a message filter configuration stored in the data memory based on the message priority indication, the use context associated with the analytical device, and the identified type of analytical device status data associated with the message priority indication, and update a data structure defining the message filter configuration, based at least in part on the record associated with the identified type of the analytical device status data and the use context, and wherein the communications interface is configured to communicate the data structure defining the message filter configuration, or a portion thereof, to a second analyzer network comprising a second analytical device.

16. An apparatus configured to host an analytical device management system for processing data from one or more analytical devices, the apparatus comprising:

a communications interface, wherein the communications interface is configured to receive a plurality of items of analytical device status data from at least one analytical device in a second analyzer network, and to obtain, via a communications network, a message filter configuration configured to filter at least one of a plurality of messages received from the second analyzer network, wherein the message filter configuration is generated by:

receiving a message priority indication indicating a first priority assigned to a first analytical device status data generated by a first analytical device in the second analyzer network;

identifying a type of the first analytical device status data associated with a message priority indication, wherein the first analytical device status data comprises condition data associated with the analytical device including one or more of a hardware heartbeat, a specific hardware fault, overheating information, lid jam information, reagent information, device temperature information, or count of assays performed;

determining, based at least in part on network configuration information associated with the second analyzer network, a use context associated with the first analytical device;

determining a record for the message filter configuration associated with the identified type of the analytical device status data and the use context, based at least in part on the message priority indication; and configuring the message filter configuration in a first data memory based on the record associated with the identified type of analytical device status data and the use context;

a second data memory, wherein the communications interface is configured to receive, via the communications network, the message filter configuration and to store it in the second data memory;

a display interface; and a processor coupled to the communications interface and the second data memory, wherein the processor is configured to filter at least one item of analytical device status data in the plurality of items of analytical device status data according to the message filter configuration stored in the second data memory to generate a filtered plurality of analytical device status data and wherein the display interface is configured to display the filtered plurality of analytical device status data.

17. A networked system for analytical device management, the networked system comprising:

a first set of one or more analytical devices configured to analyze patient medical samples and to generate analytical device status data;

a first analytical device management system configured to receive analytical device status data from one or more analytical devices comprised in the first set of one or more analytical devices;

an apparatus configured to host a data processing agent for processing data received from the first analytical device management system and/or the first set of one or more analytical devices;

a second set of one or more analytical devices configured to analyze patient medical samples;

a second analytical device management system configured to receive analytical device status data from one or more analytical devices comprised in the second set of one or more analytical devices; and a communication network configured to communicatively connect the first analytical device management system, the apparatus configured to host the data processing agent, and second analytical device management system, wherein the apparatus is configured to:

receive a message priority indication generated by the first analytical device management system and/or a first analytical device in a first analyzer network, identify a type of the analytical device status data associated with the message priority indication, wherein the analytical device status data comprises condition data associated with the first analytical device including one or more of a hardware heartbeat, a specific hardware fault, overheating information, lid jam information, reagent information, device temperature information, or count of assays performed, determining, based at least in part on network configuration information associated with the first analyzer network, a use context associated with the first analytical device management system and/or the first analytical device;

determine a record for a message filter configuration based on the identified type of the analytical device status data, the use context, and the message priority indication, update a data structure defining the message filter configuration, based at least in part on the record associated with the identified type of the analytical device status data and the use context; and communicate the data structure defining the message filter configuration, or a portion thereof, to the second analytical device management system and/or the second set of one or more analytical devices, and wherein the second analytical device management system and/or at least one analytical device in the second set of one or more analytical devices is configured to receive a further item of analytical device status data from within a second analyzer network, and to display the further item of analytical device status data according to a priority assigned in the message filter configuration.

18. The networked system according to claim 17, wherein the identified type of data of analytical device status data comprises feedback information associated with the first analytical device.

* * * * *